(12) United States Patent
Evans et al.

(10) Patent No.: US 6,743,906 B1
(45) Date of Patent: Jun. 1, 2004

(54) PPP2R1B IS A TUMOR SUPPRESSOR

(75) Inventors: Glen A. Evans, San Marcos, CA (US); Steven Siqing Wang, The Woodlands, TX (US); Edward D. Esplin, Dallas, TX (US); Jia Ling Li, Dallas, TX (US); Liying Huang, Guang Dong (CN)

(73) Assignee: Board of Regents, The University of Texas, Austin, TX (US)

( * ) Notice: Subject to any disclaimer, the term of this patent is extended or adjusted under 35 U.S.C. 154(b) by 0 days.

(21) Appl. No.: 09/410,416

(22) Filed: Oct. 1, 1999

Related U.S. Application Data

(60) Provisional application No. 60/102,952, filed on Oct. 2, 1998.

(51) Int. Cl.$^7$ .......................... C07H 21/04; A01N 43/04

(52) U.S. Cl. .................... 536/23.5; 536/24.1; 536/24.2; 514/44

(58) Field of Search ............................. 536/23.5, 24.1, 536/24.2; 514/44

(56) References Cited

U.S. PATENT DOCUMENTS

| | | | | |
|---|---|---|---|---|
| 4,554,101 A | | 11/1985 | Hopp ....................... | 260/112.5 |
| 4,683,195 A | | 7/1987 | Mullis et al. ................... | 435/6 |
| 4,800,159 A | | 1/1989 | Mullis et al. ............ | 435/172.3 |
| 4,873,191 A | | 10/1989 | Wagner et al. ........... | 435/172.3 |
| 4,883,750 A | | 11/1989 | Whiteley et al. .............. | 435/6 |
| 4,683,202 A | | 11/1990 | Mullis ......................... | 435/91 |
| 5,252,479 A | | 10/1993 | Srivastava ............... | 435/235.1 |
| 5,279,721 A | | 1/1994 | Schmid ................... | 204/182.8 |
| 5,354,855 A | | 10/1994 | Cech et al. ................ | 536/24.1 |
| 5,417,978 A | * | 5/1995 | Tari et al. | |
| 5,643,748 A | * | 7/1997 | Snodgrass et al. ....... | 435/252.3 |
| 5,672,344 A | | 9/1997 | Kelley et al. .............. | 424/93.2 |

FOREIGN PATENT DOCUMENTS

| | | |
|---|---|---|
| EP | 273085 | 7/1988 |
| EP | 329 822 | 8/1989 |
| GB | 2202328 | 3/1988 |

OTHER PUBLICATIONS

Hemmings et al. (Biochemistry, vol. 29, No. 13, 1990, pp. 3166–3173).*
Baysal, B.E. et al. Genomic organization and precise physical location of proein phosphatase 2A regulatory subunit A beta isoform gene on chromosome band 11q23. Gene, 217: 107–116, Sep. 1998.*
Bosch, M. et al. The PR55 and PR65 subunits of protein phosphatase 2A from *Xenopus laevis*. Molecular cloning and developmental regulation of expression. European J. Biochem. 230: 1037–1045, 1995.*
Arai et al., "A yeast artificial chromosome contig and Not1 restriction map that spans the tumor suppressor gene(s) locus, 11q22.2–q23.3," *Genomics*, 35:196–206, 1996.

Brower et al., "Growth of cell lines and clinical specimens of human non–small cell lung cancer in a serum–free defined medium," *Cancer Res.*, 46: 798–806, 1986.
Carney et al., "Establishment and identification of small cell lung cancer cell lines having classic and variant features," *Cancer Res.*, 45: 2913–2923, 1985.
Carter et al., "Allelic loss of chromosomes 16q and 10q in human prostate cancer," *Proc. Natl. Acad. Sci. USA*, 87:8751–8755, 1990.
Davis et al., "Refinement of two chromosome 11q regions of loss of heterozygosity in ovarian cancer," *Cancer Res.*, 56:741–744, 1996.
El–Naggar et al., "Microsatellite instability in preinvasive and invasive head and neck squamous carcinoma," *Amer. J. Pathology*, 148(6):2067–2072, 1996.
Evans et al., "Factitious breast cancer family history: a new form of Munchausen syndrome?," Abstract, *Am. J. Hum. Genet,.* 59:A66(342), 1996.
Fujiki and Suganuma, "Tumor promotion by inhibitors of protein phosphates 1 and 2A: the okadaic acid class of compounds," *Adv. Cancer Res.*, 61:143–194, 1993.
Gustafson et al., "Loss of heterozygosity on the long arm of chromosome 11 in colorectal tumours," *British Journal of Cancer*, 70:395–397, 1994.
Hampton et al., "Loss of heterozygosity in cervical carcinoma: subchromosomal localization of a putative tumor–suppressor gene to chromosome 11q22–q24," *Proc. Natl Acad Sci U S A*, 91:6953–6957, 1994.
Heriche et al., "Regulation of protein phosphate 2A by direct interaction with casein kinase 2α," *Science*, 276:952–955, 1997.
James et al., "A radiation hybrid map of 506 STS markers spanning human chromosome 11," *Nat Genet* 8(1):70–76, 1994.
Kawabe et al., "HOX11 interacts with protein phosphatases PP2A and PP1 and disrupts a G2/M cell–cycle checkpoint," *Nature*, 385:454–459, 1997.
Lee et al., "INH, a negative regulator of MPF, is a form of protein phosphatase 2A," *Cell*, 64:415–423, 1991.
Li et al., "*PTEN*, a putative protein tyrosine phosphate gene mutated in human brain, breast, and prostate cancer," *Science* 275:1943–1947, 1997.
Marshall, "Specificity of receptor tyrosine kinase signaling: transient versus sustained extracellular signal–regulated kinase activation," *Cell* 80, 179–185, 1995.

(List continued on next page.)

Primary Examiner—Gary B. Nickol
(74) Attorney, Agent, or Firm—Fulbright & Jaworski

(57) ABSTRACT

The present invention identifies the PPP2R1B gene, as a human tumor suppressor gene. Sequencing of the PPP2R1B revealed that the gene is located on human chromosome 11q22–24 and that gene were mutated in tumors and tumor cell lines, leading to the classification of this gene as a tumor suppressor. Further analyses have demonstrated the presence of a number of mutations in the gene in lung, colon, breast and cervical cancer cells. Methods for diagnosing and treating cancers related to this tumor suppressor also are disclosed.

8 Claims, 11 Drawing Sheets

OTHER PUBLICATIONS

Negrini et al., "Suppression of tumorigenicity of breast cancer cells by microcell–mediated chromosome transfer: studies on chromosomes 6 and 11," *Cancer Res.* 54:1331–1336, 1994.

Pallas et al., "Polyoma small and middle T antigens and SV40 small t antigen form stable complexes with protein phosphatase 2A," *Cell* 60:167–176, 1990.

Rasio et al., "Loss of heterozygosity at chromosomes 11q in lung adenocarcinoma: identification of three independent regions," *Cancer Research*, 55:3988–3991, 1995.

Ruediger et al., "Molecular model of the A subunit of protein phosphatase 2A: interaction with other subunits and tumor antigens," *J. Virol.* 68(1):123–129, 1994.

Satoh et al., "Suppression of tumorigenicity of A549 lung adenocarcinoma cells by human chromosomes 3 and 11 introduced via microcell–mediated chromosome transfer," *Mol Carciogenesis* 7:157–164, 1993.

Saxon, "Introduction of human chromosome 11 via microcell transfer controls tumorigenic expression of HeLa cells," *EMBO J,.* 5:3461–3466, 1986.

Sontag et al., "The interaction of SV40 small tumor antigen with protein phosphate 2A stimulates the map kinase pathway and induces cell proliferation," *Cell*, 75:887–897, 1993.

Steck et al., "Identifcation of a candidate tumor suppressor gene, *MMAC1*, at chromosome 10q23.3 that is mutated in multiple advanced cancers," *Nat. Genet.*, 15:356–362, 1997.

Tomlinson et al., "Allele loss on chromosome 11q and microsatellite instability in malignant melanoma," *Eur J Cancer*, 10:1797–1802, 1996.

Walter and Mumby, "Protein serine/threonine phosphates and cell transformations," *Biochim. Biophys. Acta.*, 1155:207–226, 1993.

Weissman et al., "Introduction of a normal human chromosome 11 into a Wilms' tumor cell line controls its tumorigenic expression," *Science*, 236:175–180, 1987.

\* cited by examiner

```
PP2AA   human                              MAAADGD
PP2AA   human                    MAGASELSGPGAAGGDGD
PP2AA   pig                    NSAGAAAPGTGPVAAGGDGD
PP2AA   xenopus                            MAGADGD (1)  DSLYPIAVLIDELRNEDVQLRLNSIKKLSTIALALGVER
     DSLYPIAVLIDELRNEDVQLRLNSIKKLSTIALALGVER
     DSLYPIAVLIDELRNEDVQLRLNSIKKLSTIALALGVER
     DSLYPIAVLIDELRNEDVQLRLNSIKKLSTIALALGVER (2)  TRSELLPFLTDTIYDEDEVLLALAEQLGTFTTLVGGPE
     TRSELLPFLTDTIYDEDEVLLALAEQLGNETSLVGGPD
     TRTELLPFLTDTIYDEDEVLLALAEQLGNFTGLVGGPD
     TRTELLPFLTDTIYDEDEVLLALAEQLGSFTSLVGGSE (3)  YVHCLLPPLESLATVEETVVRDKAVESLRAISHEHSPSD
     FAHCLLPPLENLATVEETVVRDKAVESLRQISQEHTPVA
     FAHCLLPPLESLATVEETVVRDKAVESLRQISQEHTPVA
     FVHCLLPPLESLATVEETVVRDKAVDSLRKISNEHSPVD (4)  LEAHFVPLVKRLAGGDWFTSRTSACGLFSVCYPRVSSA
     LEAYFVPLVKRLASGDWFTSRTSACGLFSVCYPRASNA
     LEAHFVPLVKRLASGDWFTSRTSACGLFSVCYPRASNA
     LEAHFVPLVKRLASGDWFTSRTSACGLFSVCYPRVSST (5)  VKAELRQYFRNLCSDDTPMVRRAAASKLGEFAKVLELDN
     VKAEIRQDFRSLCSDDTPMVRRAAASKLGEFAKVLELDS
     VKAEIRQHFRSLCSDDTPMVRRAAASKLGEFAKVLELDS
     VKAEIRQHFRNLCSDDTPIVRRAAASKLGEFAKVLELEY (6)  VKSEIIPMFSNLASDEQDSVRLLAVEACVNIAQLLPQED
     VKSEIVPLFTSLASDEQDSVRLLAVEACVSIAQLLSQDD
     VKSEIVPLFTNLASDEQDSVRLLAVEACVSIAQLLSQDD
     VKNDLIPLFTNLASDEQDSVRLLAVEACVNIAELLPEED (7)  LEALVMPTLRQAAEDKSWAVRYMVADKFTELQKAVGPEI
     LETLVMPTLRQAAEDKSWRVRYMVADRFSELQKAMGPKI
     LEALVMPTLRQAAEDKSWRVRYMVADKFSELQRAVGPKI
     LEAHVLPTLRQATEDKSCGVRYMVADKFSELQKAVGPEI
```

FIG. 1B-1

```
(8)  TKTDLVPAFQNLMKDCEAEVRAAASHKVKEFCENLSADGRENV
     TLNDLIPAFQNLLKDCEAEVRAAAAHKVKELGENLPLEGRETI
     TLNDLIPAFQNLLKDCEAEVRAAAAHKVKELCENLPIEGRETI
     TXNDLVPAFQNLLKDCEAEVRAAAAHKVKEFCENLPDDGRETI (9)  IMSQILPCIKELVSDANQHVKSALASVIMGLSPTLGKDN
     IMNQILPYIKELVSDTNQHVKSALASVIMGLSTILGKEN
     IMNQILPCIKELVSDTNQHVKSALASVIMGLSTILGKEN
     IMSHILPYVKELVSDTNQHVKSALPSVIMGLSTILGKDN

(10) TIEHLLPLFLAQLKDECPEVRLNIISNLDCVNEVIGIRQ
     TIEHLLPLFLAQLKDECPDVRLNIISNLDCVNEVIGIRQ
     TIEHLLPLFLAQLKDECPEVRLNIISNLDCVNEVIGIRQ
     TIEHLLPLFLAQLKDECPEVRLNIISNLDCVNEVIGIRQ

(11) LSQSLLPAIVELAEDAKWRVRLATIEYMPLLAGCLGVEF
     LSQSLLPAIVELAEDAKWRVRLATIEYMPLLAGCLGVEF
     LSQSLLPAIVELAEDAKWRVRLATIEYMPLLAGCLGVEF
     LSQSLLPAIVELAEDTKWRVRLATIEYMPLLAGCLGVEF

(12) FDEKLNSLCMAWLVDHVYAIREAATSNLKKLVEKFGKEW
     FDEKLNSLCMAWLVDHVYAIREAATNNLVKLVQKFGTEW
     FDEKLNSLCMAWLVDHVYAIREAATNNLVKLVQKFGTEW
     FDEKLNSLCMAWLVDHVYAIREAATNNLMKLVEKFGAEW

(13) AHATILPKVLAMSGDPNYLHRMTTLFCINVLSEVCGQDI
     AQNTIVPKVLVMANEPNYLHRMTTLFCTNALSEACGQEI
     AQNTIVPKVLVMANDPNYLHRMTTLFCINVLSEACGQEI
     AQNTIVPKVLAMANDPNYLHRMTTLFCVNALSEACGKEI

(14) TTKHMLPIVLRMAGDPVANVRENVAKSLQKIGPILDNST
     TTKQMLPIVLKMAGDCANVRFNVAKSLQKIGPILDTNA
     TTKQMLPIVLKMAGDVANVRFNVAKSLQKIGPILDTDA
     TTKLMLPIVLKMAGDQDANVRFNVARSLQRIGPVLDDTT

(15) LQSEVKPILEKLTQDQDVEVKYFAQEALTVLSLA
     LQGENKPVLQKLGQDEDMDVKYFAQEATSVLALA
     LQEENKPVLQKLGQDEDMDVKYFAQEATSVLAEA
     LQSEVKPILLKLGQDEDMDVKYFAQEAMTVLALA
```

FIG. 1B-2

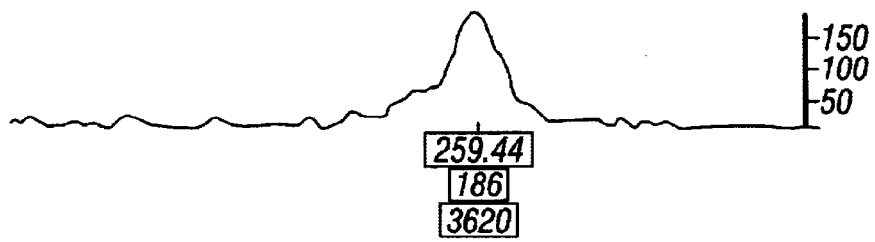
lung cancer cell line from patient No. 7 D11S1792
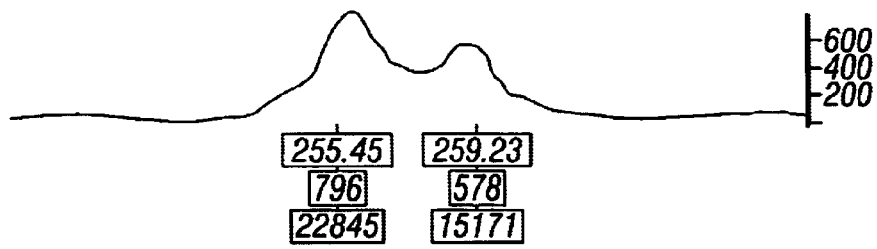
lymphoblastoid cell line from patient No. 7 D11S1792
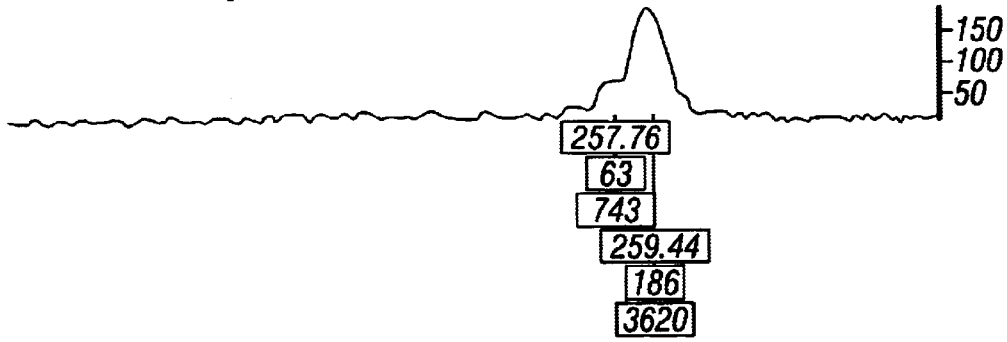
20e  4 Blue  lung cancer cell line from patient No. 20 D11S1885
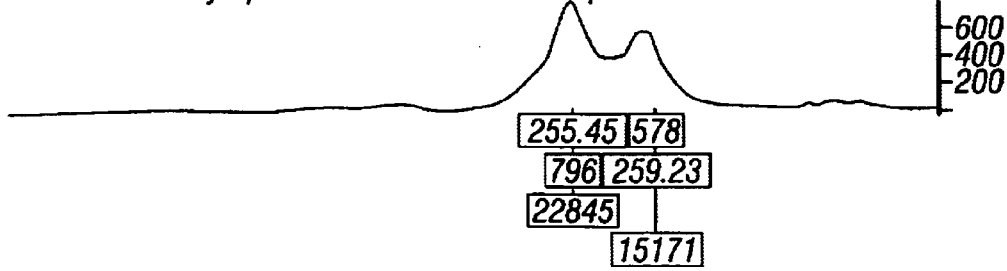
20N  12 Blue  lymphoblastoid cell line from patient No. 20 D11S1885
FIG. 4A-1

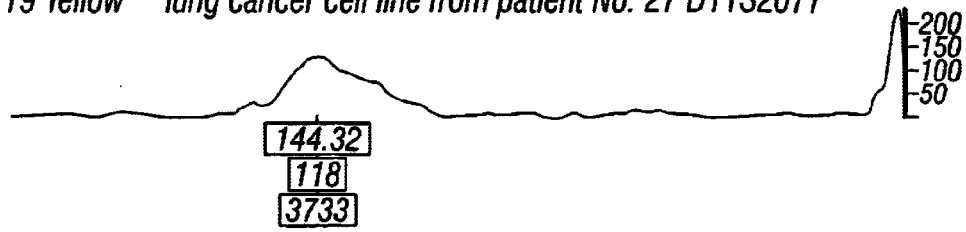
27e  19 Yellow  lung cancer cell line from patient No. 27 D11S2077
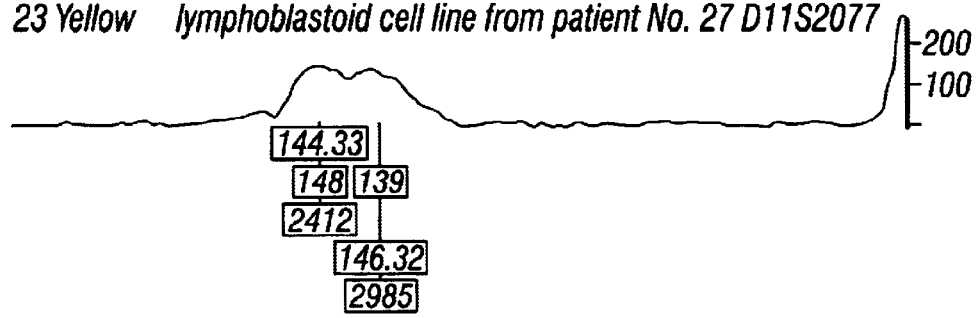
27N  23 Yellow  lymphoblastoid cell line from patient No. 27 D11S2077
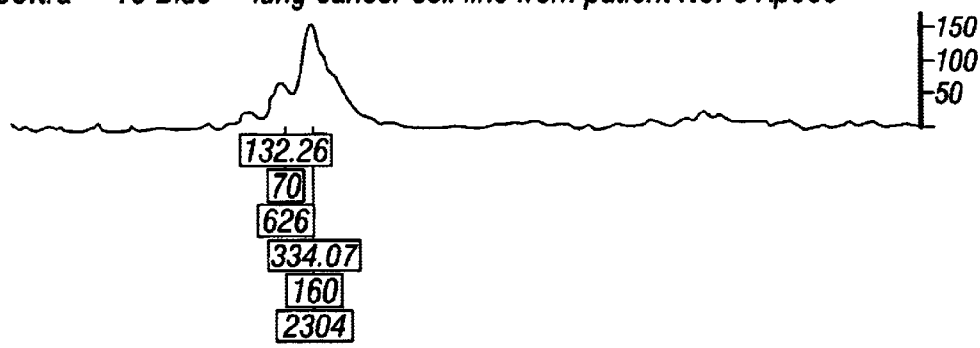
3C.tra  19 Blue  lung cancer cell line from patient No. 3 Apoc3
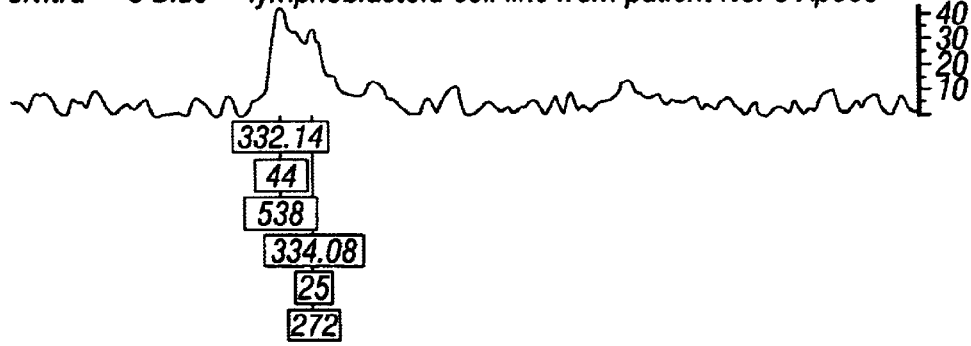
3N.tra  3 Blue  lymphoblastoid cell line from patient No. 3 Apoc3
FIG. 4A-2

PPP2R1B IS A TUMOR SUPPRESSOR

CROSS-REFERENCE TO RELATED APPLICATIONS

The present application claims the benefit of U.S. Provisional Patent Application Ser. No. 60/102,952, filed Oct. 2, 1998. The government owns rights in the present invention pursuant to grant number HG-00202-08 from the National Institutes of Health.

BACKGROUND OF THE INVENTION

1. Field of the Invention

The present invention relates to the fields of oncology, genetics and molecular biology. More particular the invention relates to the identification, on human chromosome 11, of a tumor suppressor gene. Defects in this gene are associated with the development of cancers, such as lung carcinoma.

2. Description of Related Art

Oncogenesis was described by Foulds (1958) as a multi-step biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

Lung cancer is one of the most fatal and frequent human cancers in the United States (Parker et al., 1997). Identification of the multiple tumor-suppressor genes involved in pathogenesis of lung cancer is a critical step in the development of new diagnostic methods and tumor-specific treatments. A large body of evidence suggests that chromosome 11 may harbor at least one tumor-suppressor gene(s) involved in lung cancer (Rasio et al., 1995) and a variety of other cancers including colon (Gustafson et al., 1994), breast (Carter et al., 1994), cervical (Hampton et al., 1994), head and neck (El-Naggar et al., 1996), ovarian cancers (Davis et al., 1996) and melanoma (Tomlinson et al., 1996). That this region of the chromosome has suppressor oncogene activity has been shown by the introduction of a normal chromosome 11, or a derivative t(X,11) chromosome containing 11pter-q23, into tumorigenic cells lines reversing the tumorigenic potential. Tumor suppressing activity has been demonstrated on chromosome 11q23 using lung (Satoh et al., 1993), Wilms tumor (Weissman et al., 1987), breast (Negrini et al., 1994) and cervical carcinoma cell lines (Saxon et al., 1986).

Since allelic loss of chromosome 11q22–24 has been implicated in a variety of cancers, significant effort has been applied to detailed mapping of this region of the genome using polymorphic markers. Using this approach, it has been possible to define a common and restricted region of loss of heterozygosity (LOH) region between markers STMY1 at 11q22 and ApoC3 at 11q23 in these neoplasms (Arai et al., 1996). These studies suggest the presence of functional tumor-suppressor gene(s) on chromosome 11q22–q24 localized centromeric to the t(X;11) translocation breakpoint at 11q23.

Despite all of this information, the identity of the gene (or genes) involved with the 11q23-related tumor suppression remains elusive. Without identification of a specific gene and deduction of the protein for which it codes, it is impossible to begin developing an effective therapy targeting this product. Thus, it is an important goal to isolate the tumor suppressor(s) located in this region and determine its structure and function.

SUMMARY OF THE INVENTION

In specific embodiments, the present invention provides an isolated polynucleotide comprising a region, or the complement thereof, encoding a tumor suppressor designated PPP2R1B or an allelic variant or mutant thereof. More particularly, the tumor suppressor coding region is selected from the group consisting of Xenopus, porcine and human. In yet more preferred embodiments, the tumor suppressor coding region is human. In those embodiments in which the polynucleotide is a mutant tumor suppressor, the mutant may comprise a deletion mutation, an insertion mutation, a frameshift mutation, a nonsense mutation, a missense mutation or splice mutation. In certain embodiments, the mutant is a splice mutant. More specifically, the splice mutation is in intron 8. In more defined embodiments, the splice mutation results from a mutation in intron 8.

Yet another preferred embodiments contemplated is one in which the mutation is a change from $A_{1540}$ to $G_{1540}$ as compared to the wild-type tumor suppressor. More particularly, the mutation results in a change from ASP to GLY at position 504 of the tumor suppressor. In specific embodiments, the mutation results in a change from a loss of heterozygosity. More specific embodiments contemplate a mutation that results in a change from $G_{51}$ to $C_{51}$ in the tumor suppressor. In yet another embodiment, the mutation results in a change from GLY to ARG at amino acid residue 8 of the tumor suppressor. In certain other embodiments, the mutation is a germline mutation. In yet another embodiments, the mutation is a change from $G_{298}$ to $A_{298}$ in the tumor suppressor. More particularly, the mutation results in a change from GLY to ASP at amino acid 90 of the tumor suppressor. In another contemplated embodiment, the mutation is a change from $A_{1056}$ to $G_{1056}$ in the tumor suppressor. Also contemplated is a mutation that results in a change from LYS to GLU at amino acid 343 of the tumor suppressor. In another example, the mutation is a change from $C_{222}$ to $T_{222}$ in the tumor suppressor. Yet a further mutation results in a change from PRO to SER at amino acid 65 of the tumor suppressor. In still another embodiments, the mutation is a change from $T_{1663}$ to $C_{1663}$ in the tumor suppressor. An additional mutation results in a change from VAL to ALA at amino acid 545 of the tumor suppressor. Another mutation is one in which there is a change from $T_{331}$ to $C_{331}$ in the tumor suppressor. Another specific embodiments is one in which the mutation results in a change from LEU to PRO at amino acid 101 of the tumor suppressor. Yet another mutation is a change from $T_{1372}$ to $C_{1372}$ in the tumor suppressor. More particularly, the mutation results in a change from VAL to ALA at amino acid 448 of the tumor suppressor. In specific embodiments, the mutation is an in-frame deletion of bases 717 to 1583. More particularly this mutation results in a truncated tumor suppressor expression. Yet more specifically, the truncated tumor suppressor lacks amino acids 230 to 518 of the wild-type tumor suppressor. In specific embodiments, the mutation is a deletion of nucleotides 1584 through to 1726. In other embodiments, the mutation results in a frameshift in tumor suppressor expression. In still another embodiments, the tumor suppressor has a frameshift between amino acids 519 and 601. In certain embodiments, the mutation is a deletion of nucleotides 1057 to 1191. More particularly, the mutation results in a truncated tumor suppressor expression. Specifically, the truncated tumor suppressor may lack amino acids 344 to 388 of the wild-type tumor suppressor. In other particularly preferred embodiments, the mutation is a deletion of nucleotides 1315 through to 1505. More particularly, the mutation results in a frameshift in tumor suppressor expression. Yet more particularly, the tumor suppressor has a frameshift between amino acids 422 and 601.

In specific embodiments, the tumor suppressor has the amino acid sequence of SEQ ID NO:1. In other embodiments, the tumor suppressor has the amino acid sequence of SEQ ID NO:2. In yet a further embodiments, the polynucleotide sequence comprises the coding sequence of SEQ ID NO:4 or the complement thereof. In certain specific embodiments, the polynucleotide sequence comprises a porcine PPP2R1B or the complement thereof. In other exemplary embodiments, the polynucleotide sequence comprises a Xenopus PPP2R1B or the complement thereof. In particularly defined embodiments, the polynucleotide may be selected from the group consisting of genomic DNA, complementary DNA and RNA. More particularly, the polynucleotide may be a complementary DNA and further comprise a promoter operably linked to the region, or the complement thereof, encoding the tumor suppressor. In still further embodiments, the polynucleotide further may comprise a polyadenylation signal operably linked to the region encoding the tumor suppressor. In additional embodiments the polynucleotide also may comprise an origin of replication. In specific embodiments, the polynucleotide is a viral vector selected from the group consisting of retrovirus, adenovirus, herpesvirus, vaccinia virus and adeno-associated virus. In further embodiments, the polynucleotide is packaged in a virus particle. In additional embodiments, the polynucleotide is packaged in a liposome.

In certain specific embodiments the polynucleotide is of a size selected from the group consisting of about 100 bases, about 200 bases, about 300 bases, about 400 bases about 500 bases, about 600 bases about 700 bases, about 800 bases, about 900 bases, about 1000 bases, about 1200 bases, about 1500 bases, about 1800 bases, about 1922 bases and about 2000 bases.

Also provided herein is an isolated polypeptide encoding a tumor suppressor designated as PPP2R1B. In specific embodiments the tumor suppressor has the amino acid sequence as set forth in SEQ ID NO:1. In other particular embodiments, the tumor suppressor has an amino acid sequence as set forth in SEQ ID NO:2. In still further embodiments, the tumor suppressor has an amino acid sequence as set forth in SEQ ID NO:3.

Also provided herein is an isolated peptide having between about 10 and about 50 consecutive residues of a tumor suppressor designated as PPP2R1B. It is contemplated that the peptide may be conjugated to a carrier molecule. More particularly, the carrier molecule is selected from the group consisting of KLH and BSA. In specific embodiments, the tumor suppressor may have the amino acid sequence as set forth in SEQ ID NO: 1, SEQ ID NO:2, SEQ ID NO:3 or any sequence variant thereof.

Also contemplated herein is a monoclonal antibody that binds immunologically to a tumor suppressor designated as PPP2R1B. In particularly embodiments the antibody does not bind immunologically to other human polypeptides. In other embodiments, the antibody binds to a non-human PPP2R1B and does not bind to human PPP2R1B. In some embodiments, the antibody further comprises a detectable label. More particularly, the label may be selected from the group consisting of a fluorescent label, a chemiluminescent label, a radiolabel and an enzyme.

Also contemplated is a hybridoma cell that produces a monoclonal antibody that binds immunologically to a tumor suppressor designated as PPP2R1B. Another embodiment contemplates a polyclonal antisera, antibodies of which bind immunologically to a tumor suppressor designated as PPP2R1B. In specific embodiments the antisera is derived from an animal other than human, pig or Xenopus.

The present invention further provides a method of diagnosing a cancer comprising the steps of obtaining a sample from a subject; and determining the expression of a functional PPP2R1B tumor suppressor in cells of the sample. In specific embodiments, the cancer may be selected from the group consisting of brain, lung, liver, spleen, kidney, lymph node, small intestine, pancreas, blood cells, colon, stomach, breast, endometrium, prostate, testicle, ovary, skin, head and neck, esophagus, bone marrow and blood cancer. In more specific embodiments, the cancer is a lung cancer, colon cancer, breast cancer or cervical cancer. In preferred embodiments, the sample is a tissue or fluid sample. In certain embodiments, the determining comprises assaying for a nucleic acid from the sample. More particularly, the method further comprises subjecting the sample to conditions suitable to amplify the nucleic acid. Alternative embodiments contemplate that the determining comprises contacting the sample with an antibody that binds immunologically to a PPP2R1B. More specifically, the method further comprises subjecting proteins of the sample to ELISA. In other embodiments, the method further comprises the step of comparing the expression of PPP2R1B with the expression of PPP2R1B in non-cancer samples. In specific embodiments, the comparison involves evaluating the level of PPP2R1B expression. In other embodiments, the comparison involves evaluating the structure of the PPP2R1B gene, protein or transcript. More particularly, the evaluating is an assay selected from the group consisting of sequencing, wild-type oligonucleotide hybridization, mutant oligonucleotide hybridization, SSCP, PCR™ and RNase protection. In more specific embodiments, the evaluating is wild-type or mutant oligonucleotide hybridization and the oligonucleotide is configured in an array on a chip or wafer.

Also the present invention provides a method for altering the phenotype of a tumor cell comprising the step of contacting the cell with a tumor suppressor designated PPP2R1B under conditions permitting the uptake of the tumor suppressor by the tumor cell. In particular embodiments, the tumor cell is derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. More particularly, the phenotype is selected from the group consisting of proliferation, migration, contact inhibition, soft agar growth and cell cycling. In preferred embodiments, the tumor suppressor is encapsulated in a liposome.

Also provided is a method for altering the phenotype of a tumor cell comprising the step of contacting the cell with a nucleic acid (i) encoding a tumor suppressor designated PPP2R1B and (ii) a promoter active in the tumor cell, wherein the promoter is operably linked to the region encoding the tumor suppressor, under conditions permitting the uptake of the nucleic acid by the tumor cell. In specific embodiments, the nucleic acid is a viral vector selected from the group consisting of retrovirus, adenovirus, adeno-associated virus, vaccinia virus and herpesvirus. More particularly, the nucleic acid is encapsulated in a viral particle.

Also contemplated is a method for treating cancer comprising the step of contacting a tumor cell within a subject with a tumor suppressor designated PPP2R1B under conditions permitting the uptake of the tumor suppressor by the tumor cell. In specific embodiments, the subject is a human.

Also provided is a method for treating cancer comprising the step of contacting a tumor cell within a subject with a nucleic acid (i) encoding a tumor suppressor designated PPP2R1B and (ii) a promoter active in the tumor cell, wherein the promoter is operably linked to the region encoding the tumor suppressor, under conditions permitting the uptake of the nucleic acid by the tumor cell.

Another aspect of the present invention contemplates a transgenic mammal in which both copies of the gene encoding PPP2R1B are interrupted or replaced with another gene.

Also provided is a method of determining the stage of cancer comprising the steps of obtaining a sample from a subject; and determining the expression a functional PPP2R1B tumor suppressor in cells of the sample. In certain embodiments, the cancer is a lung cancer. In particular embodiments, the determining comprises assaying for a PPP2R1B nucleic acid or polypeptide in the sample.

Another aspect of the present invention is to provide a method of predicting tumor metastasis comprising the steps of obtaining a sample from a subject; and determining the expression a functional PPP2R1B tumor suppressor in cells of the sample. In specific embodiments, the cancer is distinguished as metastatic and non-metastatic. In particular aspects, the determining comprises assaying for a PPP2R1B nucleic acid or polypeptide in the sample.

Another embodiment provides a method of screening a candidate substance for anti-tumor activity comprising the steps of providing a cell lacking functional PPP2R1B polypeptide; contacting the cell with the candidate substance; and determining the effect of the candidate substance on the cell. In specific embodiments, the cell is a tumor cell. More particularly, the tumor cell has a mutation in the coding region of PPP2R1B. In specific embodiments, the mutation is a deletion mutant, an insertion mutant, a frame-shift mutant, a nonsense mutant, a missense mutant or splice mutant. In certain aspects, the determining comprises comparing one or more characteristics of the cell in the presence of the candidate substance with characteristics of a cell in the absence of the candidate substance. More specifically, the characteristic is selected from the group consisting of PPP2R1B expression, phosphatase activity, proliferation, metastasis, contact inhibition, soft agar growth, cell cycle regulation, tumor formation, tumor progression and tissue invasion. In defined embodiments, the candidate substance is a chemotherapeutic or radiotherapeutic agent. In other preferred embodiments, the candidate substance is selected from a small molecule library. In specific embodiments, the cell is contacted in vitro. In alternative embodiments, the cell in contacted in vivo.

Also provided is a method of screening a candidate substance for anti-kinase activity comprising the steps of providing a having PPP2R1B polypeptide comprising at least one serine/threonine kinase site; contacting the cell with the candidate substance; and determining the effect of the candidate substance on the phosphorylation of the site. Similar assays may be performed for anti-phosphatase activ-ity. In specific embodiments, the determining comprises comparing one or more characteristics of the cell in the presence of the candidate substance with characteristics of a cell in the absence of the candidate substance. More particularly, the characteristic is selected from the group consisting of phosphorylation status of PPP2R1B, PPP2R1B expression, phosphatase activity, proliferation, metastasis, contact inhibition, soft agar growth, cell cycle regulation, tumor formation, tumor progression and tissue invasion.

The present invention further provides a method of diagnosing a subject predisposed to cancer comprising the steps of obtaining a sample from a subject; and determining the expression a functional PPP2R1B gene product in cells of the sample. More particularly, the cancer is selected from the group consisting of lung, colon, breast and cervical cancer. In specific embodiments, the cells are selected from the group consisting of breast cells, lung cells, ovarian cells, cervical cells, and endometrial cells. In additional embodiments, the sample is a tissue or fluid sample. Particularly, the determining may comprise assaying for a nucleic acid from the sample. In certain embodiments, the method further comprises subjecting the sample to conditions suitable to amplify the nucleic acid. It is contemplated that the determining may comprise contacting the sample with an antibody that binds immunologically to a PPP2R1B. In certain embodiments, the method further may comprise subjecting proteins of the sample to ELISA. In other embodiments, the method further comprises the step of comparing the expression of PPP2R1B with the expression of PPP2R1B in normal samples. It is contemplated that the comparison may involve evaluating the level of PPP2R1B expression. Alternatively, the comparison may involve evaluating the structure of the PPP2R1B gene, protein or transcript. In specific embodiments, the evaluating is an assay selected from the group consisting of sequencing, wild-type oligonucleotide hybridization, mutant oligonucleotide hybridization, SSCP, PCR™ and RNase protection. More particularly, the evaluating is wild-type or mutant oligonucleotide hybridization and the oligonucleotide is configured in an array on a chip or wafer. In specifically defined embodiments, the sample comprises a mutation in the coding sequence of PPP2R1B.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

As stated above, a number of different groups have shown evidence of a tumor suppressing activity associated with human chromosome 11. Despite this considerable amount of work, the identity of the gene or genes responsible for this activity has not been determined. Previous investigations used a functional approach involving transfer of chromosomes or chromosomal fragments suspected of harboring tumor suppressor gene(s) into tumorigenic cells. These efforts allowed definition of the biological activity of putative tumor suppressor gene(s) and aided in the localization of such activity. The present invention shows that the t(X;11) translocation breakpoint maps to a region between D11S1340 and D11S1341 on 11q23–24. Previously, three distinct commonly deleted regions on 11q22–q24 were identified in lung cancers (Rasio et al., 1995). One of the regions is bracketed by polymorphis markers D11S940 and CD3D, which is overlapped with the region between STMY1 and ApoC3 (FIG. 1). The common region lying between D11S940 and ApoC3 also is located centromeric to t(X;11) breakpoint. Therefore, in order to more clearly define regions of allelic loss in lung cancers, the pattern of LOH in the region between D11S940 and ApoC3 were studied using 17 microsatellite markers typed using automated genoytping techniques. This data demonstrate that LOH in this region is frequent (71.4%) and defines two distinct minimal regions of loss suggesting at least two distinct suppressor oncogenes.

Figure 1A:
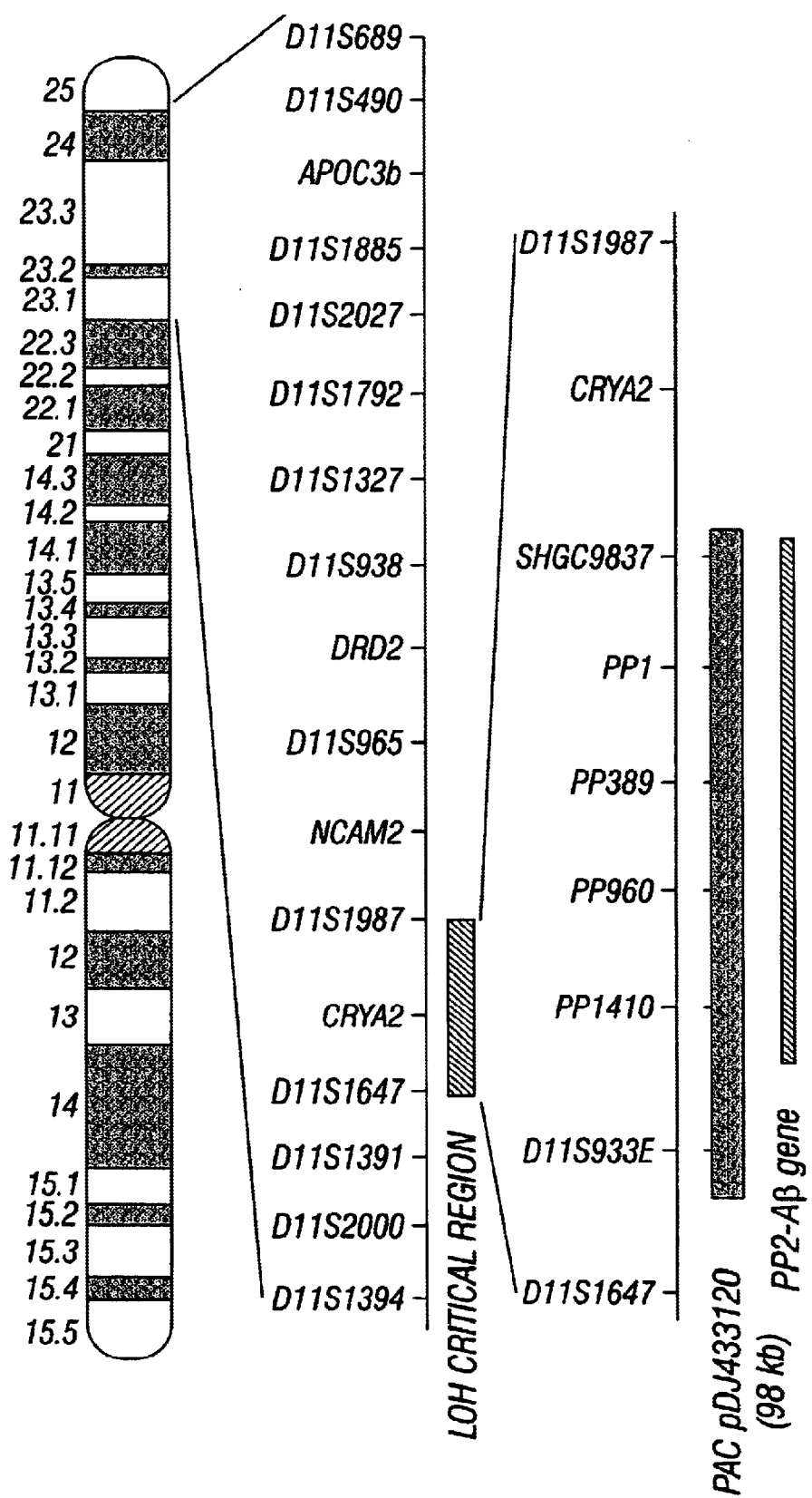
FIG. 1. (A) Physical map of chromosome 11q23–24 showing PPP2R1B and the LOH critical region. Polymorphic markers from chromosome 11 radiation hybrid maps were used for LOH analysis. Expansion of the map and high resolution mapping was done by PAC clone isolation (Ioannou et al., 1994). Markers PP1410, PP960, PP389 and PP1 were derived from portions of an EST sequence (Genbank accession number M6525). (B) The predicted amino acid sequence of PP2A-Aβ (SEQ ID NO:5), determined from the sequence of PPP2R1B. Alignment of human PP2A-Aβ (SEQ ID NO:5, first sequence in alignment), with pig PP2A-Aβ (SEQ ID NO:3, third sequence in alignment), Xenopus PP2A-Aβ (SEQ ID NO:2, fourth sequence in alignment) and human PP2A-Aα (SEQ ID NO: 1, second sequence in alignment). Boxed amino acids represent highly conserved residues defining 15 internal repeats (Ruediger et al., 1994). Shaded amino acids represent mutations found in lung and colon tumors are indicated in the human PP2A-Aβ sequence. Sequence alignment was carried out using Multiple Sequence Alignment (InfoMax, Bethesda, Md. and MegaAlign (DNAStar Inc, Madison, Wis.). Portions of the human PPP2R1B sequence were determined previously (Hemmings et al., 1990; GenBank accession number M65254). The complete sequence of the human PPP2R1B gene has been deposited in GenBank (accession number AF087438).

To identify the tumor suppressor genes on chromosome 11 that are inactivated in lung cancer, the inventors mapped the t(X;11) breakpoint relative to regions of frequent LOH and defined a minimum critical region between D11S1394 and D11S689 (FIG. 1A). This region of chromosome 11q23 demonstrated high frequency LOH in a variety of cancers including lung and colon. Evaluation of LOH in 28 lung cancer and paired normal cell lines revealed allelic loss in 71% of the cancer cell lines. Two polymorphic DNA markers, D11S1647 and D11S1987, showed allelic loss in 42.9% and 46.2%, of the cancer cell lines, respectively (Evans et al., 1996), and both markers were lost in 28.6% of the cell lines.

Based on these results, the region between D11S1394 and D11S689, and especially between D11S1647 and D11S1987, was systematically surveyed for candidate tumor-suppressor genes. Over 100 candidate genes and expressed sequence tag (EST) markers were identified from a human chromosome 11 radiation hybrid map (ftp.well.ox.ac.uk) and the Human Gene Map (available at .ncbi.nlm.nih.gov/SCIENCE96/ResTools.html; a www. should precede the previous URL). One of the EST sequences (M65254) was found to correspond to a subunit of the serine/threonine protein phosphatase 2A (PP2A). PP2A is an important regulatory enzyme that down-regulates the mitogen-activated protein kinase (MAPK) cascade, relays signals for cell proliferation and has been linked to carcinogenesis (Marshall, 1995). The PP2A holoenzyme exists in several trimeric forms consisting of a 36 kD core catalytic subunit PP2A-C, a 65 kD structural/regulatory component, PP2A-A, and a variable regulatory subunit, PP2A-B, which confers distinct properties on the holoenzyme. Each subunit exists as multiple isoforms encoded by different genes so that there are many forms of the PP2A trimer differing expression patterns and specificity. The gene identified at chromosome 11q23, denoted PPP2R1B according to standardized nomenclature, encodes the β isoform of the structural/regulatory A subunit, PP2A-Aβ. PP2A-Aβ is necessary for interaction of the catalytic PP2A-C and variable PP2A-B subunits and is critical for phosphatase activity (Walter and Mumby, 1993).

According to the present invention, the inventors have found that the PPP2R1B subunit is associated with a tumor suppressor activity and that mutation in this tumor suppressor are present in lung, colon, breast, and cervical tumors and other cancers. Further, the present invention, for the first time, provides the complete protein and cDNA sequence of the PPP2R1B sununit. The present invention has employed various approaches in this identification, These approaches, described in greater detail in the following Examples, included (i) identification of homozygous deletions in a series of human cancer cell lines; (ii) determination of a consistent region(s) of retention in clones suppressed for tumorigenicity; and (iii) allelic deletion studies on various grades of tumor and corresponding normal samples. With the gene in hand, it now becomes possible to exploit the information encoded by the gene to develop novel diagnostic and therapeutic approaches related to human cancer.

II. The PPP2R1B Tumor Suppressor

According to the present invention, there has been identified a tumor suppressor, encoded by a gene in the 11q22–24 locus, and designated here as PPP2R1B. This molecule is capable of suppressing tumor phenotypes in various cancers. The term tumor suppressor is well-known to those of skill in the art. Examples of other tumors suppressors are PTEN, p53, Rb and p16, to name a few. While these molecules are structurally distinct, they form a group of functionally-related molecules, of which PPP2R1B is a member. The uses in which these other tumor suppressors now are being exploited are equally applicable here.

In addition to the entire PPP2R1B molecule, the present invention also relates to fragments of the polypeptide that may or may not retain the tumor suppressing (or other) activity. Fragments, including the N-terminus of the molecule may be generated by genetic engineering of translation stop sites within the coding region (discussed below). Alternatively, treatment of the PPP2R1B molecule with proteolytic enzymes, known as proteases, can produces a variety of N-terminal, C-terminal and internal fragments. Examples of fragments may include contiguous residues of the PPP2R1B. sequence given in SEQ ID NO:1, SEQ ID NO:2 or SEQ ID NO:3, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural Features of the Polypeptide

The gene for PPP2R1B encodes the β isoform of the a subunit of the serine/threonine protein phosphatase 2A (PP2A), was identified as a putative human tumor suppressor gene. The phosphatase is a 601-amino-acid protein with extensive homology to the PP2A-Aβ subunits of pig and Xenopus, and to the human. The PP2A holoenzyme exists in several trimeric forms consisting of a 36 kD core catalytic subunit PP2A-C, a 65 kD structural/regulatory component, PP2A-A, and a variable regulatory subunit, PP2A-B, which confers distinct properties on the holoenzyme. Each subunit exists as multiple isoforms encoded by different genes so that there are many forms of the PP2A trimer differing expression patterns and specificity. The gene identified at chromosome 11q23, denoted PPP2R1B according to standardized nomenclature, encodes the β isoform of the structural/regulatory A subunit, PP2A-Aβ. PP2A-Aβ is necessary for interaction of the catalytic PP2A-C and variable PP2A-B subunits and is critical for phosphatase activity.

Protein phosphatases generally are divided into two categories - serine/threonine phosphatases and tyrosine phosphatases. Certain of the tyrosine phosphatases also have activity against phosphoserine and phosphothreonine. The PP2A-Aβ phosphatase is a serine/threonine phosphatase. The reaction can be represented as a two-step chemical process: phosphoryl transfer to the enzyme accompanied by rapid release of dephosphorylated product; and hydrolysis of the thiol-phosphate intermediate concomitant with rapid release of phosphate. To form the catalytically competent component complex, the enzyme binds and reacts with the dianion of phosphate-containing substrate. On the enzyme, an aspartic acid must be protonated and the nucleophilic cysteine must be unprotonated (thiolate anion) for phosphoryl transfer to the enzyme. Phosphatases are known to have kinase sites, and the phosphatase activity of these enzymes can be modulated by phosphorylation at these sites.

The interaction between kinases and phosphatases, and the various phosphorylation states of polypeptides, have been demonstrated as important features in cell physiology. Through a variety of different mechanisms, kinases and phosphatases act in different pathways within cells that are involved in signaling, energy storage and cell regulation. Since the identification of an intrinsic tyrosine kinase function in the transforming protein src (Collett & Erickson, 1978), the role of phosphorylation, particularly on tyrosine residues, has been demonstrated to be critical in the control of cellular proliferation and the induction of cancer (Hunter, 1991; Bishop, 1991). The roles that protein phosphatases play in growth regulation, as well as in many other biological and biochemical activities, have been correlated with the phosphorylation state of biologically important molecules (Cohen, 1994).

Protein phosphatases are postulated to be involved in the suppression of cellular growth and cancer development by antagonizing protein kinases, many of which act as oncoproteins. A gene encoding a putative protein tyrosine phosphatase, PTEN/MMAC1, was recently shown to be mutated in human brain, breast, and prostate cancer (Li et al., 1997, Steck et al., 1997). PP2A also plays an important role in cell cycle checkpoint control (Lee et al., 1991), inhibits nuclear telomerase activity (Li et al., 1997) and is a well known target for chemical tumor promoters (Fujiki and M. Suganuma, 1993), DNA tumor viruses, oncogenes, and components of cell growth control. Polyoma virus T antigen and SV40 small T antigen bind to PP2A-A, displacing PP2A-B and inhibiting PP2A phosphatase activity which is thought to mediate viral transformation (Pallas et al., 1990, Sontag et al., 1993). The HOX11 oncogene interacts with PP2A, inhibiting activity and disrupting a G2/M cell-cycle checkpoint (Kawabe et al., 1997). Casein kinase 2α inhibits cellular transformation by Ras and suppresses cell growth by enhancing PP2A activity (Heriche et al., 1997).

B. Functional Aspects

When the present application refers to the function of PPP2R1B or "wild-type" activity, it is meant that the molecule in question has the ability to inhibit the transformation of a cell from a normally regulated state of proliferation to a malignant state, i.e., one associated with any sort of abnormal growth regulation, or to inhibit the transformation of a cell from an abnormal state to a highly malignant state, e.g., to prevent metastasis or invasive tumor growth. Other phenotypes that may be considered to be regulated by the normal PPP2R1B gene product are angiogenesis, adhesion, migration, cell-to-cell signaling, cell growth, cell proliferation, density-dependent growth, anchorage-dependent growth and others. Determination of which molecules possess this activity may be achieved using assays familiar to those of skill in the art. For example, transfer of genes encoding PPP2R1B, or variants thereof, into cells that do not have a functional PPP2R1B product, and hence exhibit impaired growth control, will identify, by virtue of growth suppression, those molecules having PPP2R1B function.

As stated above, PPP2R1B is a serine/threonine phosphatase. Also another characteristic of phosphatases is that they possess kinase targets that are located within the molecule. Because other tumor suppressors have been identified with this type of activity, it will be desirable to determine the phosphatase function in the tumor suppressing role of PPP2R1B. Thus, the PPP2R1B may have a kinase and a phosphatase activity. This also may be a fruitful approach to developing screening assays for the absence of PPP2R1B function or in the development of cancer therapies, for example, in targeting the phosphatase function of PPP2R1B, targeting the substrate upon which PPP2R1B acts, and/or targeting the kinase or kinases which act upon PPP2R1B.

C. Variants of PPP2R1B

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In particular aspects it is contemplated that one of skill in the art will employ standard technologies well known to those of skill in the art to produce the mutants,. Specifically contemplated will be N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Proteins expressed from such mutant can be assayed for apoptosis inhibiting and/or chaperone function as described throughout the specification. Similar techniques are employed in internal deletion mutants, however, in internal deletion mutants are generated by using two suitably placed restriction sites, thereby allowing a precisely defined deletion to be made, and the ends to be religated as above.

Also contemplated are partial digestions mutants. In such instances, one of skill in the art would employ a "frequent cutter", that cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

Once general areas of the gene are identified as encoding particular protein domains, point mutagenesis may be employed to identify with particularity which amino acid residues are important in particular activities associated with PPP2R1B. Thus one of skill in the art will be able to generate single base changes in the DNA strand to result in an altered codon and a missense mutation.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of PPP2R1B, but with altered and even improved characteristics.

D. Domain Switching

As described in the examples, the present inventors have identified putative porcine and Xenopus homologs of the human PPP2R1B gene. In addition, mutations have been identified in PPP2R1B which are believed to alter its function. These studies are important for at least two reasons. First, they provide a reasonable expectation that still other homologs, allelic variants and mutants of this gene may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule. One way in which this information can be exploited is in "domain switching."

Domain switching involves the generation of chimeric molecules using different but, in this case, related polypeptides. By comparing the porcine, Xenopus and human sequences for PPP2R1B with the PPP2R1B of other species, and with mutants and allelic variants of these polypeptides, one can make predictions as to the functionally significant regions of these molecules. It is possible, then, to switch related domains of these molecules in an effort to determine the criticality of these regions to PPP2R1B function. These molecules may have additional value in that these "chimeras" can be distinguished from natural molecules, while possibly providing the same function.

Based on the sequence identity, at the amino acid level, of the mouse, dog and human sequences, it may be inferred that even small changes in the primary sequence of the molecule will affect function. Further analysis of mutations and their predicted effect on secondary structure will add to this understanding.

Another structural aspect of PPP2R1B that provides fertile ground for domain switching experiments is the serine/threonine phosphatase-like domain and the putative serine/threonine phosphorylation sites. This domain may be substituted for other phosphatase domains in order to alter the specificity of this function. A further investigation of the homology between PPP2R1B and other phosphatases is warranted by this observation.

E. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

One particular fusion of interest would include a deletion construct lacking the phosphatase site of PPP2R1B but containing other regions that could bind the substrate molecule. Fusion to a polypeptide that can be used for purification of the substrate-PPP2R1B complex would serve to isolated the substrate for identification and analysis.

Examples of fusion protein expression systems include the glutathione S-transferase (GST) system (Pharmacia, Piscataway, N.J.), the maltose binding protein system (NEB, Beverley, Mass.), the FLAG system (IBI, New Haven, Conn), and the 6×His system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation.

In still further systems, it is possible to create fusion protein constructs to enhance immunogenicity of a PPP2R1B fusion construct to increase immunogenicity are well known to those of skill in the art, for example, a fusion of PPP2R1B with a helper antigen such as hsp70 or peptide sequences such as from Diptheria toxin chain or a cytokine such as IL2 will be useful in eliciting an immune response. In other embodiments, fusion construct can be made which will enhance the targeting of the PPP2R1B related compositions to a specific site or cell. For example, fusing PPP2R1B or a PPP2R1B type protein to a ligand will be an effective means to target the composition to a site expressing the receptor for such a ligand. In this manner the PPP2R1B or PPP2R1B related composition may be delivered into a cell via receptor mediated delivery. The PPP2R1B protein can be attached covalently or fused to a ligand. This can be used as a mechanics for delivery into a cell. The ligand with the protein attached may then be internalized by a receptor bearing cell.

Other fusion systems produce polypeptide hybrids where it is desirable to excise the fusion partner from the desired polypeptide. In one embodiment, the fusion partner is linked to the recombinant PPP2R1B polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

F. Purification of Proteins

It will be desirable to purify PPP2R1B or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

The present invention also describes smaller PPP2R1B-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tarn et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

U.S. Pat. No. 4,554,101 (incorporated herein by reference) also teaches the identification and preparation of epitopes from primary amino acid sequences on the basis of hydrophilicity. Through the methods disclosed in Hopp, one of skill in the art would be able to identify epitopes from within any amino acid sequence encoded by any of the DNA sequences disclosed herein.

H. Antigen Compositions

The present invention also provides for the use of PPP2R1B proteins or peptides as antigens for the immunization of animals relating to the production of antibodies. It is envisioned that either PPP2R1B, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding PPP2R1B. Genes for the human, canine and murine PPP2R1B molecule have been identified. The present invention is not limited in scope to these genes, however, as one of ordinary skill in the could, using these nucleic acids, readily identify related homologs in various other species (e.g., rat, rabbit, monkey, gibbon, chimp, ape, baboon, cow, pig, horse, sheep, cat and other species). The finding of porcine and Xenpus homologs for this gene makes it likely that other species more closely related to humans will, in fact, have a homolog as well.

In addition, it should be clear that the present invention is not limited to the specific nucleic acids disclosed herein. As discussed below, a "PPP2R1B gene" may contain a variety of different bases and yet still produce a corresponding polypeptide that is functionally indistinguishable, and in some cases structurally, from the human, porcine and Xenopus genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of PPP2R1B.

A. Nucleic Acids Encoding

The human DNA for encoding PPP2R1B disclosed in SEQ ID NO:4. Additionally, the porcine and Xenopus genes that PPP2R1B sequences SEQ ID NO:3 and SEQ ID NO:2 respectively, also form part of the present invention. Nucleic acids or polynucleotides according to the present invention may encode an entire PPP2R1B gene, a domain of PPP2R1B that expresses a tumor suppressing or phosphatase function, or any other fragment of the PPP2R1B sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given PPP2R1B from a given species may be represented by natural variants that have slightly different nucleic acid sequences but, nonetheless, encode the same protein (see Table 1 below).

As used in this application, the term "a nucleic acid encoding a PPP2R1B" refers to a nucleic acid molecule that has been isolated free of total cellular nucleic acid. In preferred embodiments, the invention concerns a nucleic acid sequence essentially as set forth in SEQ ID NO:4. The term "as set forth in SEQ ID NO:4" means that the nucleic acid sequence substantially corresponds to a portion of SEQ ID NO:4. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:4 will be sequences that are "as set forth in SEQ ID NO:4." Sequences that are essentially the same as those set forth in SEQ ID NO:4 may also be functionally defined as sequences that are capable of hybridizing to a nucleic acid segment containing the complement of SEQ ID NO:4 under standard conditions.

The DNA segments of the present invention include those encoding biologically functional equivalent PPP2R1B proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NO:4. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:4 under relatively stringent conditions such as those described herein. Such sequences may encode the entire PPP2R1B protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 350, 400, 450, 500, 550, 600, 650, 700, 750, 800, 850, 900, 950, 1000, 1100, 1150, 1200, 1250, 1300, 1500, 1922, 2000, 3000, 4000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

One method of using probes and primers of the present invention is in the search for genes related to PPP2R1B or, more particularly, homologs of PPP2R1B from other species. The existence of a porcine homolog strongly suggests that other homologs of the human PPP2R1B will be discovered in species more closely related, and perhaps more remote, than pig. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of PPP2R1B in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express the PPP2R1B polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Promoters. Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ECDYSONE SYSTEM™ (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 2).

TABLE 2

Tissue specific promoters

| Tissue | Promoter |
| --- | --- |
| Pancreas | insulin |
|  | elastin |
|  | amylase |
|  | pdr-1 pdx-1 |
|  | glucokinase |
| Liver | albumin PEPCK |
|  | HBV enhancer |
|  | alpha fetoprotein |
|  | apolipoprotein C |
|  | alpha-1 antitrypsin |
|  | vitellogenin, NF-AB |
|  | Transthyretin |

TABLE 2-continued

Tissue specific promoters

| Tissue | Promoter |
| --- | --- |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha1acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, radiation-inducible (e.g., EGR (Joki et al., 1995)), Alpha-inhibin, RNA pol III tRNA met and other amino acid promoters, U1 snRNA (Bartlett et al., 1996), MC-1, PGK, β-actin and α-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

Enhancers. Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 3 and Table 4). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 3

EHHANCER/PROMOTER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin

TABLE 3-continued

EHHANCER/PROMOTER

Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Abe Leukemia Virus

TABLE 4

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Polyadenylation Signals. Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

IRES. In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (poliovirus and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

Adenoviruses. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1 -deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1 -coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al, (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Herpesvirus. Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1987). The expression of a genes, the first set of genes to be expressed after infection, is enhanced by the virion protein number 16, or α-transducing factor (Post et al., 1981; Batterson and Roizman, 1983; Campbell et al., 1983). The expression of α genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. A virulent variants of HSV have been developed and are readily available for use in gene therapy contexts (U.S. Pat. No. 5,672,344).

Adeno-Associated Virus. Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al., 1997a). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al. (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

Vaccinia Virus. Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (E1 roy-Stein et al., 1989).

Non-Viral transfer. In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al, 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-9 mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products.

However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

IV. Generating Antibodies Reactive With PPP2R1B

In another aspect, the present invention contemplates an antibody that is immunoreactive with a PPP2R1B molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to PPP2R1B-related antigen epitopes. Additionally, it is proposed that monoclonal antibodies specific to the particular PPP2R1B of different species may be utilized in other useful applications.

In general, both polyclonal and monoclonal antibodies against PPP2R1B may be used in a variety of embodiments. For example, they may be employed in antibody cloning protocols to obtain cDNAs or genes encoding other PPP2R1B. They may also be used in inhibition studies to analyze the effects of PPP2R1B related peptides in cells or animals. Anti-PPP2R1B antibodies will also be useful in immunolocalization studies to analyze the distribution of PPP2R1B during various cellular events, for example, to determine the cellular or tissue-specific distribution of PPP2R1B polypeptides under different points in the cell cycle. A particularly useful application of such antibodies is in purifying native or recombinant PPP2R1B, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat.

No. 4,196,265, incorporated herein by reference. Typically, this technique involves immunizing a suitable animal with a selected immunogen composition, e.g., a purified or partially purified PPP2R1B protein, polypeptide or peptide or cell expressing high levels of PPP2R1B. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference. Human antibodies may also be produced by transforming B cells with EBV and subsequent cloning of secretors as described by Hoon et al, (1993).

Antibody conjugates in which a PPP2R1B antibody is linked to a detectable label or a cytotoxic agent form further aspects of the invention. Diagnostic antibody conjugates may be used both in vitro diagnostics, as in a variety of immunoassays, and in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA). Fluorescent labels include rhodamine, fluorescein isothiocyanate and renographin.

V. Diagnosing Cancers Involving PPP2R1B

The present inventors have determined that alterations in PPP2R1B are associated with malignancy. Therefore, PPP2R1B and the corresponding gene may be employed as a diagnostic or prognostic indicator of cancer. More specifically, point mutations, deletions, insertions or regulatory pertubations relating to PPP2R1B may cause cancer or promote cancer development, cause or promoter tumor progression at a primary site, and/or cause or promote metastasis. Other phenomena associated with malignancy that may be affected by PPP2R1B expression include angiogenesis and tissue invasion.

A. Genetic Diagnosis

One embodiment of the instant invention comprises a method for detecting variation in the expression of PPP2R1B. This may comprises determining that level of PPP2R1B or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, cervix, stomach, prostate, testicle, ovary, skin, head and neck, esophagus, bone marrow, blood or other tissue. In particular, the present invention relates to the diagnosis of in lung, colon, breast and cervical cancers.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have PPP2R1B-related pathologies. In this way, it is possible to correlate the amount or kind of PPP2R1B detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of PPP2R1B produced, both by altering the transcription of the gene or in destabilizing or otherwise altering the processing of either the transcript (mRNA) or protein.

A cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

The results presented herein demonstrate that various tumors contain mutation sin PPP2R1B. These mutations are summarized in Table 5. For example, H1450 cells had a 1.8 kb PCR amplification product representing the wild type PPP2R1B and a second 1 kb product. Sequencing of the 1 kb amplification product revealed an internal in-frame deletion of 867 bp, which is predicted to produce a truncated PP2A-Aβ lacking of amino acids 230 to 518. Further, there was an $A_{1540} \rightarrow G$ transition changing a highly conserved $Asp_{504} \rightarrow Gly$ in the 1.8 kb PCR product. Therefore, both alleles of PPP2R1B are altered and possibly inactivated, whereas the matched lymphoblastoid cell line from the same patient, BL7, contains no detectable alterations.

In H220 cells, one of the PPP2R1B alleles had a 143 bp deletion resulting in a frameshift and loss of 83 amino acids at the COOH terminus of PP2A-Aβ (Table 5). An additional 18 alterations in PPP2R1B in 11 tumor derived cell lines and primary tumors including lung and colon were identified (Table 5). The alterations include deletions, frameshifts and point mutations leading to non-conservative amino acid substitutions (Table 5). For example, a $G_{298} \rightarrow A$ transition is seen in cell line H2009, which changes a conserved $Gly_{90} \rightarrow Asp$, as well as a wild type PPP2R1B allele. The matched lymphoblastoid cell line, (BL2009), has both $G_{298} \rightarrow A$ and wild type coding sequences, suggesting that the lung cancer patient from which these cells are derived harbors a germline mutation in the PPP2R1B gene. Although it is possible that this alteration is a polymorphism rather than a mutation, it was not detected in 200 other normal and malignant cell lines.

Also found in two separate tumors was a $Gly_{90} \rightarrow Asp$ mutation, this mutation was not present in surrounding normal tissue, suggesting a hot spot for mutation. The colon adenocarcinoma T25 had two alterations in the same PPP2R1B allele. Many of the mutations identified in conserved amino acids within the repeating PP2A-Aβ sequence necessary for binding to the catalytic C subunit (Ruediger et al., 1994). In particular, deletions and frameshifts which alter repeats 11–15 are likely to affect binding of PP2A-Aβ and enzyme activity (Ruediger et al., 1994).

Point mutations were confirmed at the genomic level by sequencing PCR-amplified genomic sequence from tumor samples T64, T68, H838 and H2009. Additional non-coding alterations were detected including a G→A mutation in an exon/intron boundary, which presumably leads to a splicing error resulting in the loss of one exon, as well as the observed frameshift deletion. The PPP2R1B gene from tumors T9 and T12 each carry a point mutation inside intron 8 which could also lead to splicing errors responsible for the observed deletion. None of the mutations identified in primary tumor genomic DNA were detected in the genomic DNA from adjacent normal tissue.

These particular mutations described in the present invention and additional mutations identified by using the techniques described herein may be targeted with oligonucleotides specifically designed to identify these mutations, or with antibodies that distinguish these markers from wild-type PPP2R1B.

It is contemplated that other mutations in the PPP2R1B gene may be identified in accordance with the present invention. A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis (e.g., U.S. Pat. No. 5,190,856 incorporated herein by reference), RFLP (e.g., U.S. Pat. No. 5,324,631 incorporated herein by reference) and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of nonspecific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the PPP2R1B gene that may then be analyzed by direct sequencing.

(vi) Kit Components

All the essential materials and reagents required for detecting and sequencing PPP2R1B and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the-target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the PPP2R1B content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-PPP2R1B antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for PPP2R1B that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and H202, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The steps of various other useful immunodetection methods have been described in the scientific literature, such as, e.g., Nakamura et al. (1987; incorporated herein by reference). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. Patents concerning the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241, each incorporated herein by reference. Of course, one may find additional advantages through the use of a secondary binding ligand such as a second antibody or a biotin/avidin ligand binding arrangement, as is known in the art.

VI. Methods for Screening Active Compounds

The present invention also contemplates the use of PPP2R1B and active fragments, and nucleic acids coding therefor, in the screening of compounds for activity in either stimulating PPP2R1B activity, overcoming the lack of PPP2R1B activity or blocking the effect of a mutant PPP2R1B molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, anti-phosphatase activity, phosphorylation of PPP2R1B, dephosphorylation of PPP2R1B, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

A. In Vitro Assays

In one embodiment, the invention is to be applied for the screening of compounds that bind to the PPP2R1B molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of PPP2R1B to a natural or artificial substrate or binding partner. Competitive binding assays can be performed in which one of the agents (PPP2R1B, binding partner or compound) is labeled. Usually, the polypeptide will be the labeled species. One may measure the amount of free label versus bound label to determine binding or inhibition of binding.

As stated earlier, the present invention provides the complete sequence of PPP2R1B which was determined by using a combination of EST analysis (.ncbi.nlm.nih.gov/ncicgap; a www. should precede the URL), cDNA sequencing (Hemmings et al., 1990), and 5' rapid amplification of cDNA ends (RACE). The sequence predicts a 601-amino-acid protein with extensive homology to the PP2A-Aβ subunits of pig and Xenopus, and to the human PP2A-Aα isoform (SEQ ID NO:3, SEQ ID NO:2 and SEQ ID NO:5; respectively). Both PP2A-Aα and PP2A-Aβ are composed of 15 internal repeat sequences each consisting of two amphipathic helices necessary for binding PP2A-B and PPA2-C (Ruediger et al., 1994). Thus the binding partners for PPP2R1B may be PP2A-B and PPA2-C. Alternatively, the binding partner may be any agent that is dephosphorylated by the action of the phosphatase.

Another technique for high throughput screening of compounds is described in WO 84/03564. Large numbers of small peptide test compounds are synthesized on a solid substrate, such as plastic pins or some other surface. The peptide test compounds are reacted with PPP2R1B and washed. Bound polypeptide is detected by various methods.

Purified PPP2R1B can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the PPP2R1B active region to a solid phase.

Various cell lines containing wild-type or natural or engineered mutations in PPP2R1B can be used to study various functional attributes of PPP2R1B and how a candidate compound affects these attributes. Methods for engineering mutations are described elsewhere in this document, as are naturally-occurring mutations in PPP2R1B that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of PPP2R1B, or related pathways, may be explored. This may involve assays such as those for protein expression, enzyme function, substrate utilization, phosphorylation states of various molecules including PPP2R1B, cAMP levels, mRNA expression (including differential display of whole cell or polyA RNA) and others.

B. In Vivo Assays

The present invention also encompasses the use of various animal models. Here, the identity seen between human, porcine and Xenopus PPP2R1B provides an excellent opportunity to examine the function of PPP2R1B in a whole animal system where it is normally expressed. By developing or isolating mutant cells lines that fail to express normal PPP2R1B, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type PPP2R1B may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for PPP2R1B or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a PPP2R1B specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved PPP2R1B activity or which act as stimulators, inhibitors, agonists, antagonists or PPP2R1B or molecules affected by PPP2R1B function. By virtue of the availability of cloned PPP2R1B sequences, sufficient amounts of PPP2R1B can be produced to perform crystallographic studies. In addition, knowledge of the polypeptide sequences permits computer employed predictions of structure-function relationships.

VII. Methods for Treating PPP2R1B Related Malignancies

The present invention also involves, in another embodiment, the treatment of cancer. The types of cancer that may be treated, according to the present invention, is limited only by the involvement of PPP2R1B. By involvement, it is not even a requirement that PPP2R1B be mutated or abnormal—the overexpression of this tumor suppressor may actually overcome other lesions within the cell. Thus, it is contemplated that a wide variety of tumors may be treated using PPP2R1B therapy, including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle, cervix, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing PPP2R1B to that cell. Because the sequence homology between the human, mouse and dog genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way PPP2R1B may be utilized according to the present invention.

B. Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that PPP2R1B could serve as a target for an immune effector given that (i) it is unlikely to be expressed on the surface of the cell and (ii) that the presence, not absence, of PPP2R1B is associated with the normal state. However, it is possible that particular mutant forms of PPP2R1B may be targeted by immunotherapy, either using antibodies, antibody conjugates or immune effector cells.

A more likely scenario is that immunotherapy could be used as part of a combined therapy, in conjunction with PPP2R1B-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunoconjugates. The invention further provides immunotoxins in which an antibody that binds to a cancer marker, such as a mutant PPP2R1B, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or pseudomonas exotoxin, to mention just a few examples. The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various 'recombinant' or 'genetically engineered' forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale (available commercially from Inland Laboratories, Austin, Tex.). Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In preferred embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio)toluene).

Biologically releasable bonds are particularly important to the realization of a clinically active immunotoxin in that the toxin moiety must be capable of being released from the antibody once it has entered the target cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies, however, certain linkers are generally preferred, such as, for example, sterically hindered disulfide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane also may be employed.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the antibodies of the invention may be linked to one or more chemotherapeutic agents, such as anti-tumor drugs, cytokines, antimetabolites, alkylating agents, hormones, nucleic acids and the like, which may thus be targeted to a PPP2R1B expressing cancer cell using the antibody conjugate. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin, daunomycin, methotrexate, vinblastine. Moreover, the attachment of other agents such as neocarzinostatin, macromycin, trenimon and α-amanitin has also been described. The lists of suitable agents presented herein are, of course, merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment also may be achieved by means of an acid labile acyl hydrazone or cis aconityl linkage between the drug and the antibody, or by using a peptide spacer such as L-Leu-L-Ala-L-Leu-L-Ala, between the γ-carboxyl group of the drug and an amino acid of the antibody.

C. Protein Therapy

Another therapy approach is the provision, to a subject, of PPP2R1B polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

D. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that PPP2R1B replacement therapy could be used similarly in conjunction with chemo- or radiotherapeutic intervention. It also may prove effective to combine PPP2R1B gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a PPP2R1B expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either PPP2R1B or the other agent will be desired. Various combinations may be employed, where PPP2R1B is "A" and the other agent is "B", as exemplified below:

A/B/A B/A/B B/B/A A/A/B B/A/A A/B/B B/B/B/A B/B/ A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a PPP2R1B expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a PPP2R1B expression construct, as described above.

Agents that directly cross-link nucleic acids, specifically DNA, are envisaged to facilitate DNA damage leading to a synergistic, antineoplastic combination with PPP2R1B. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of PPP2R1B expression constructs to patients with PPP2R1B-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining PPP2R1B-targeted therapies with chemo- and radiotherapies, it also is contemplated that combination with other gene therapies will be advantageous. For example, targeting of PPP2R1B and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by-themselves in treating a PPP2R1B. In this regard, reference to chemotherapeutics and non-PPP2R1B gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal intrtumoral, circumferentially, catheterization, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VIII. Transgenic Animals/Knockout Animals

In one embodiment of the invention, transgenic animals are produced which contain a functional transgene encoding a functional PPP2R1B polypeptide or variants thereof. Transgenic animals expressing PPP2R1B transgenes, recombinant cell lines derived from such animals and transgenic embryos may be useful in methods for screening for and identifying agents that induce or repress function of PPP2R1B. Transgenic animals of the present invention also can be used as models for studying indications such as cancers.

In one embodiment of the invention, a PPP2R1B transgene is introduced into a non-human host to produce a transgenic animal expressing a human or murine PPP2R1B gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous PPP2R1B by homologous recombination between the transgene and the endogenous gene; or the endogenous gene may be eliminated by deletion as in the preparation of "knock-out" animals. Typically, a PPP2R1B gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress PPP2R1B or express a mutant form of the polypeptide. Alternatively, the absence of a PPP2R1B in "knock-out" mice permits the study of the effects that loss of PPP2R1B protein has on a cell in vivo. Knock-out mice also provide a model for the development of PPP2R1B-related cancers.

As noted above, transgenic animals and cell lines derived from such animals may find use in certain testing experiments. In this regard, transgenic animals and cell lines capable of expressing wild-type or mutant PPP2R1B may be exposed to test substances. These test substances can be screened for the ability to enhance wild-type PPP2R1B expression and or function or impair the expression or function of mutant PPP2R1B.

IX. EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should , in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials and Methods

Cell lines and DNA isolation—Twenty-eight paired lung cancer and normal lymphoblastoid cell lines derived from the same patient were utilized in this study and were described previously (Carney, D. N., et al, 1985; Brower, M., et al, 1986). These cell lines represent 11 small cell lung carcinomas and 17 non-small cell carcinomas. All cell lines were cytogenetically characterized before analysis. Cell lines were maintained in tissue culture and genomic DNA was isolated using established procedures (Sambrook, J., et al, 1989).

Microsatellite markers—Polymorphic microsatellite markers were selected from the chromosome 11 radiation hybrid map (James, et al. 1994; data access: ftp.well.ox.ac.uk). PCR oligonucleotide primers amplifying these microsatellite markers were fluorescently tagged using Tet, Fam and Hex fluorochromes for analysis using an ABI 377 automated gene sequencer. The physical positions of these microsatellite markers are determined according to the radiation hybrid map (data access: ftp.well.ox.ac.uk). For those markers that are in the same radiation hybrid bin, the relative position of the markers are determined according to an integrated map prepared in the Genome Sequencing Center of the Texas Southwestern Medical Center (data access: gestec.swmed.edu).

LOH Analyses—PCR amplification of each microsatellite marker was performed using 25–100 ng of template DNA in a final volume of 10 $\mu$M with 200 $\mu$M dNTPs and 1X PCR buffer (Boehringer Mannheim), 0.25 unit of Taq I polymerase (Boehringer Mannheim), and 0.4 mM of each oligonucleotide primers. PCR amplification was carried out for 15 seconds at 94° C., 15 seconds at 57° C. and 30 seconds at 72° C. for 33cycles using an ABI 9600 thermal cycler. PCR amplification products from multiple reactions were pooled along with internal standard size markers (Tamara 500, ABI) and loaded on a 4% urea-acrylamide gel in an ABI 377 automated DNA sequencer. To avoid human error in annotating each reaction and to maintain consistency between experiments, addition of template and primers, assembly of PCR reactions, and pooling of amplification products was carried out using a Beckman BioMek 2000 robotic workstation. Following analysis on the ABI 377 gene sequencer, the sizes and the intensities of each allele were determined using ABI Gene Scan 2.0.0 and Genotyper software 1.1.

Assessment of LOH—To facilitate assessment of LOH at each locus, PCR amplification products of paired normal and lung cancer cell lines were run in the same gel on the ABI sequencer. The sizes and relative intensities of alleles from paired normal lymphoblastoid and lung cancer-derived cell lines from the same individual were compared directly and LOH was scored when one of the two alleles was completely lost in the lung cancer cell lines relative to the corresponding lymphoblastoid cell line. Additional genetic alterations were identified when the PCR amplification products, and by inference the microsatellite alleles, of the lung cancer and matched normal cell lines were of a different length.

RT-PCR. RNA was prepared from lung cancer-derived and matched normal (lymphoblastoid) cell lines using RNA/DNA STAT60 Kit (Tel-Test, Friendswood, Tex.). Primary tumor samples were obtained from the Cooperative Tissue Network (Birmingham, Ala.) and cancer cell lines were obtained from the American Type Culture Collection (ATCC). Randomly primed cDNA was synthesized using Superscript II (GIBCO/BRL) and PCR was performed using Expand Long Template PCR System (Boehringer Mannheim). In certain cases, nested PCR was performed using 20-fold diluted amplification products from the initial PCR amplification. Primer pairs are: 5'-GGTGACCAGCAGCAGGAG-3' (SEQ ID NO:6); 5' GCTTGGATGAGATCTTGAAGG-3' (SEQ ID NO:7); 5'-GCGCATCAGAGCTCGGGACCG-3' (SEQ ID NO:8) and 5'-CCATTCTTTCTCCACCCAGTTAAGAAC-3' (SEQ ID NO:9). Amplification products were separated on 0.8% agarose gels, DNA bands were isolated with the QIA Quick Gel Extraction Kit (Qiagen, Santa Clarita, Calif.) and the DNA sequenced with the Dye Terminator Sequencing Kit (Perkin Elmer, Foster City, Calif.).

Gel-purified PCR products were cloned using the TOPO-TA Cloning Kit (InVitrogen, Carlsbad, Calif.). DNA from a single transformed colony was isolated and sequenced using automated DNA sequencing.

Immunoblotting and Immunoprecipitation. Cells were lysed, proteins separated by electrophoresis, and gels transferred to Millipore Immobilon-P membrane. Immunodetection was carried out using goat anti-human PP2A-Aβ immunoglobulin, and secondary horse radish peroxidase-conjugated donkey anti-goat immunoglobulin (Santa Cruz Biotechnology). Immunodetection was carried out using enhanced chemiluminescence (Amersham Life Sciences). Goat anti-human actin immunoglobulin was added as a control.

Cell lysates were immunoprecipitated with rabbit anti-human PP2A-C immunoglobulin (Promega) and protein G-agarose (Boehringer Mannheim). The precipitate was collected by centrifugation and the pellet washed with cold phosphate buffered saline. The precipitate was then analyzed on an 8% SDS-polyacrylamide gel. Western blot detection was carried out using purified goat anti-human immunoglobulin against PP2A-Aβ and PP2A-C, and secondary horse radish peroxidase-conjugated donkey anti-goat immunoglobulin (Santa Cruz Biotechnology).

Example 2

Localization of PPP2R1B

The precise physical location of PPP2R1B was determined by co-localizing it within P1-derived artificial chromosome (PAC) (Ioannou et al, 1994) clones that contained sequence tagged sites (STSs) on chromosome 11q22–23 (FIG 1A). PAC clone pDJ433L20 contained PPP2R1B as well as markers SHGC9837 and D11S966E, and was localized to a 15 centiRay region between markers D11S1647 and D11S1987 on 11S1987on 11q22.2 (Wang et al., 1997). Thus, the PPP2R1B gene is located in a region showing high frequency LOH (FIG. 1A).

The complete sequence of PPP2R1B was determined by a combination of EST analysis (ncbi.nlm.nih.gov/ncicgap; a www. should precede the URL), cDNA sequencing (Hemmings et al, 1990), and 5' rapid amplification of cDNA ends (RACE). Briefly, amplification was carried out using a 5' RACE Kit (Boehringer Mannheim) and oligonucleotide primers 5'-TCACTTCGGGTCCTTTCTACTCCA-3' (SEQ ID NO: 10) and 5'-CTTCATTGCGGAGCTCGTCGA- 3' (SEQ ID NO:11). Amplification conditions were as follows: 95° C. for 11 s, 59° C. for 11 s, and 72° C. for 15 s, for 33 cycles.

The sequence predicts a 601-amino-acid protein with extensive homology to the PP2A-Aβ subunits of pig and Xenopus, and to the human PP2A-Aα isoform (FIG. 1B). Both PP2A-Aα and PP2A-Aβ are composed of 15 internal repeat sequences each consisting of two amphipathic helices necessary for binding PP2A-B and PPA2-C (Ruediger et al., 1994).

Example 3

Tumors Bearing Mutations in PPP2R1B

Figure 2A:
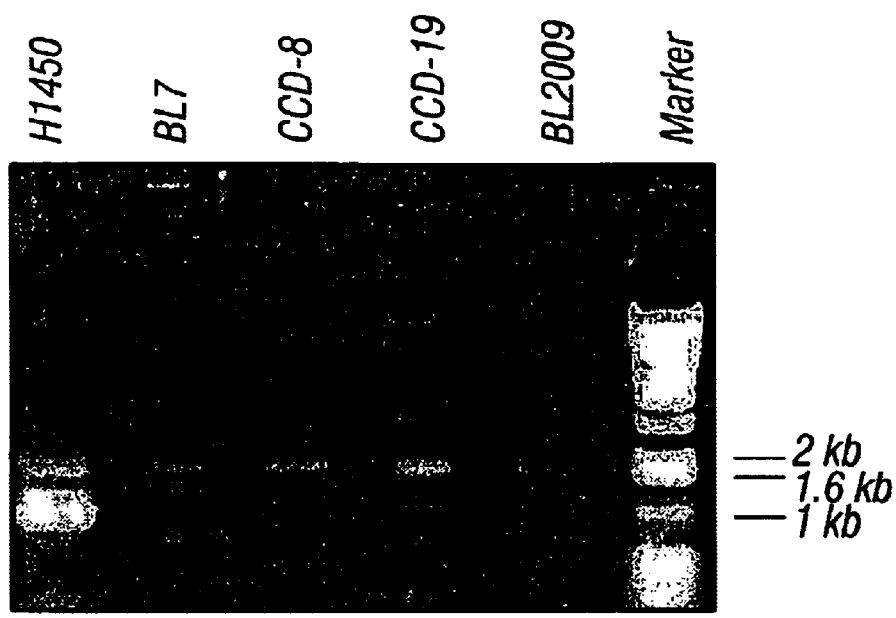
FIG. 2. Mutations of the PPP2R1B gene in cancer cell lines and primary tumors. (A) RT-PCR amplification of the coding sequence of PPP2R1B derived from lung cancer cell line H1450, matched lymphoblastoid cell line BL7, normal control lung tissues CCD-8 and CCD-19, and an unrelated lymphoblastoid cell line BL2009. PCR products were separated on an 0.8% agarose gel containing ethidium bromide. The 1.8 kb amplification product was present in all samples and the 1 kb PCR product, representing the mutant ΔPPP2R1B containing an internal deletion, is present in lysates from H1450 cells. (B) Sequencing of PPP2R1B alterations. Nucleotides 708 to 726 (GATGAACAGGCACTGT, SEQ ID NO:12) indicate an 867 bp deletion in one PPP2R1B allele of cell line H1450 compared to that of the lymphoblastoid matched control cell line BL7 (GATGAACAGGATTCAGT, SEQ ID NO:13). (C) Nucleotides 292 to 304 (TCACTGACCTAGTC, SEQ ID NO:14) show a $G_{298} \rightarrow A$ substitution in one allele of cell line H2009 but not in the other allele (TCACTGGCCTAGT, SEQ ID NO:15). (D) Nucleotides 43 to 58 (CAGAGCTCCGGACCGG, SEQ ID NO:16) show a $G_{51} \rightarrow C$ substitution in cell line H838 when compared to a normal tissue control sample CCD-8 (CAGAGCTCGGGACCGG, SEQ ID NO:17). A wild type copy of the PPP2R1B transcript was not detected in cell line H838. (E) Nucleotides 1049 to 1066 (ATATAAAGTGTCCTGA, SEQ ID NO:18) show a 135 bp deletion in one allele but not in the other allele of primary lung tumor T12 (ATATAAAGGAATTAGT, SEQ ID NO:19).
Figure 2B:
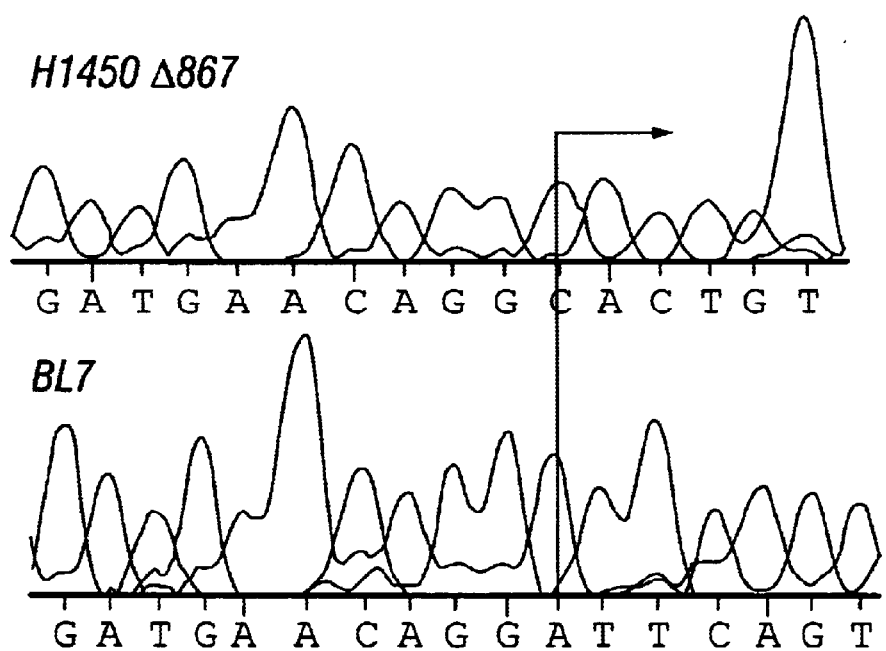

To determine if human tumors contain alterations in PPP2R1B, the coding regions were amplified by RT-PCR and direct DNA sequencing was performed in 130 cancer-derived cell lines and 70 primary tumors including lung, colon, breast, and cervical tumors. Two of these tumors generated altered amplification products suggesting PPP2R1B mutations. H1450 cells had a 1.8 kb PCR amplification product representing the wild type PPP2R1B and a second 1 kb product (FIG. 2A). Sequencing of the latter revealed an internal in-frame deletion of 867 bp, which is predicted to produce a truncated PP2A-Aβ lacking of amino acids 230 to 518 (FIG. 2B). Sequencing also revealed that the 1.8 kb PCR product contained an $A_{1540} \rightarrow G$ transition changing a highly conserved $Asp_{504} \rightarrow Gly$. Thus, both alleles of PPP2R1B are altered and possibly inactivated, whereas the matched lymphoblastoid cell line from the same patient, BL7, contains no detectable alterations. In H220 cells, one of the PPP2R1B alleles had a 143 bp deletion resulting in a frameshift and loss of 83 amino acids at the COOH terminus of PP2A-Aβ (Table 5).

TABLE 5

PPP2AB sequence alterations in lung and colon cancer.

| Tumor | Allele | cDNA alteration | Predicted effect |
|---|---|---|---|
| H1450 | 1 | Δ nts 717-1583 | Δ aa 230-518 |
| SCLC | 2 | $A_{1540} \to G$ | $Asp_{504} \to Gly$ |
| H838 | 1 | $G_{51} \to C$ | $Gly_8 \to Arg$ |
| NSCLC | 2 | wild type not detected | inactive |
| H220 | 1 | Δ nts 1584-1726 | frameshift aa 519-601 |
| SCLC | 2 | wild type | none |
| H2009 | 1 | $G_{298} \to A$ (germline) | $Gly_{90} \to Asp$ |
| NSCLC | 2 | wild type | none |
| T11 | 1 | $A_{1056} \to G$ | $Lys_{343} \to Glu$ |
| NSCLC | 2 | wild type | none |
| T9 | 1 | Δ nts 1057-1191 | Δ aa 344-388 |
| NSCLC | 2 | wild type not detected | inactive |
| T12 | 1 | Δ nts 1057-1191 | Δ aa 344-388 |
| NSCLC | 2 | $C_{222} \to T$ | $Pro_{65} \to Ser$ |
| T64 | 1 | $G_{298} \to A$ | $Gly_{90} \to Asp$ |
| NSCLC | 2 | wild type | none |
| T68 | 1 | $G_{298} \to A$ | $Gly_{90} \to Asp$ |
| NSCLC | 2 | wild type | none |
| T24 | 1 | Δ nts 1315-1505 | frameshift aa 422-601 |
| CAC | 2 | $T_{1663} \to C$ | $Val_{545} \to Ala$ |
| T25 | 1 | $T_{331} \to C; T_{1372} \to C$ | $Leu_{101} \to Pro, Val_{448} \to Ala$ |
| CAC | 2 | wild type not detected | inactive |

CAC, colon adenocarcinoma; SCSL, small cell lung carcinoma; NSCLC, non-small cell lung carcinoma; Δ, deletion; →nucleotide or amino acid alteration; "wild type not detected" indicates the probable deletion of the allele through LOH.

Figure 2C:
Figure 2C:
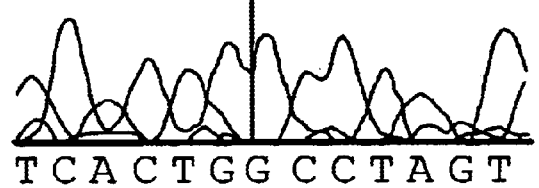
Figure 2D:
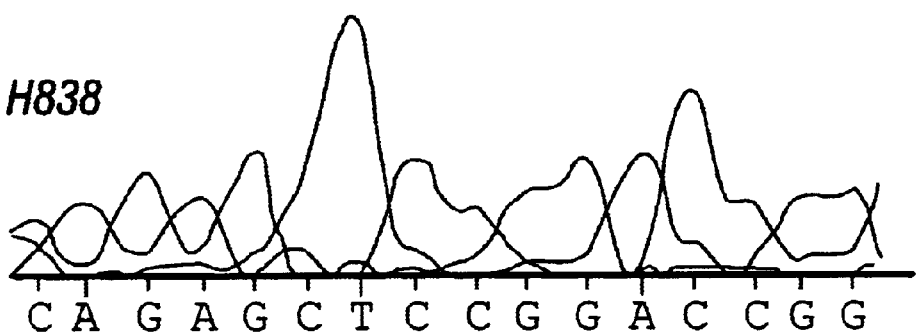
Figure 2D:
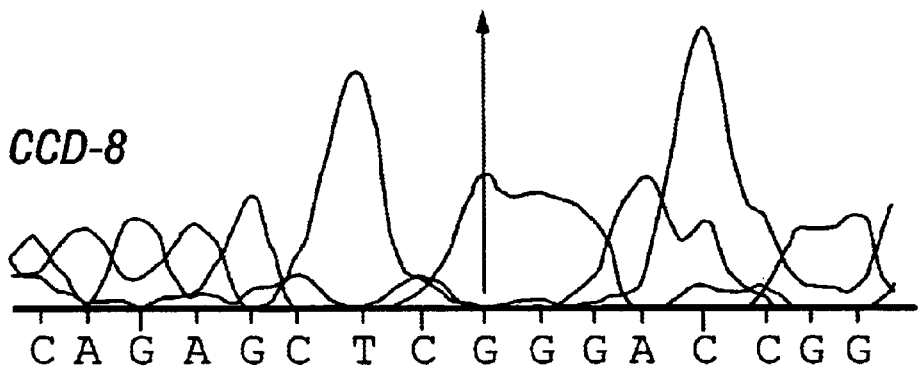
Figure 2E:
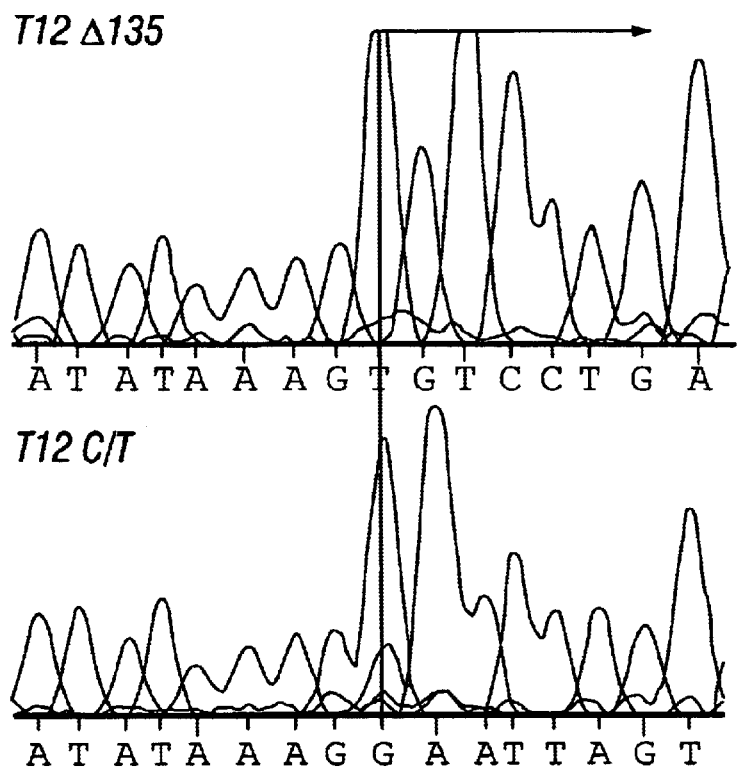

DNA sequencing of PCR amplification products revealed 18 alterations in PPP2R1B in 11 tumor derived cell lines and primary tumors including lung and colon (Table 1). The alterations include deletions, frameshifts and point mutations leading to non-conservative amino acid substitutions (Table 5). Cell line H2009 carries one allele with a $G_{298} \to A$ transition (FIG. 2C), which changes a conserved $Gly_{90} \to Asp$, as well as a wild type PPP2R1B allele. The matched lymphoblastoid cell line, (BL2009), has both $G_{298} \to A$ and wild type coding sequences, suggesting that the lung cancer patient from which these cells are derived harbors a germline mutation in the PPP2R1B gene. Although it is possible that this alteration is a polymorphism rather than a mutation, it was not detected in 200 other normal and malignant cell lines. The alteration $Gly_{90} \to Asp$ was found in two separate tumors and not in surrounding normal tissue, suggesting a hot spot for mutation. One colon adenocarcinoma T25 had two alterations in the same PPP2R1B allele (Table 5). Many of the mutations identified in conserved amino acids within the repeating PP2A-Aβ sequence necessary for binding to the catalytic C subunit (Ruediger et al., 1994) will presumably result in destabilization of the enzyme complex, and altered enzyme function. In particular, deletions and frameshifts which alter repeats 11–15 (FIG. 1B) are likely to affect binding of PP2A-Aβ and enzyme activity (Ruediger et al., 1994).

Point sequence alterations were confirmed at the genomic level by sequencing PCR-amplified genomic sequence from tumor samples T64, T68, H838 and H2009. Additional non-coding alterations were detected including a G→A mutation in an exon/intron boundary, which presumably leads to a splicing error resulting in the loss of one exon, as well as the observed frameshift deletion. The PPP2R1B gene from tumors T9 and T12 each carry a point mutation inside intron 8 which could also lead to splicing errors responsible for the observed deletion. None of the mutations identified in primary tumor genomic DNA were detected in the genomic DNA from adjacent normal tissue.

Figure 3A:
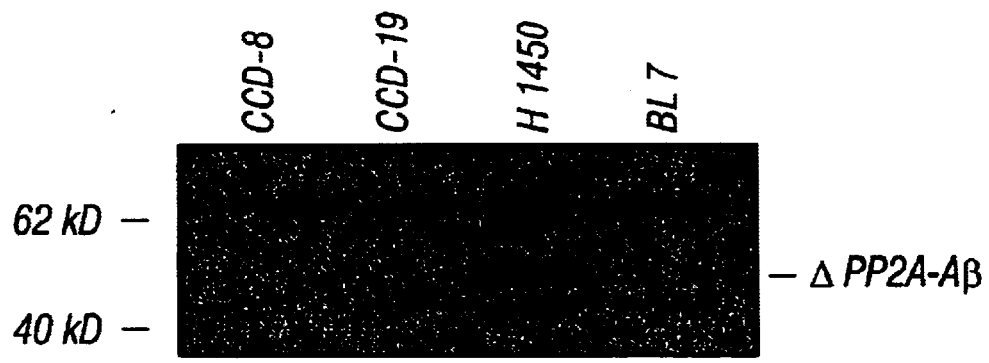
FIG. 3. (A) Identification of PP2A-Aβ proteins by immunoblotting. PP2A-Aβ, was detected in lysates of cell line H1450, BL7 lymphoblastoid control cells, and normal lung tissue samples CCD-8 and CCD-19 using anti-PP2A-Aβ immunoglobulin. The 65 kD PP2A-Aβ protein was detected in all cells tested and H1450 lysates contain an additional 45 kD band representing the mutant subunit. The 4 kD band is an actin control. (B) Co-immunoprecipitation of PP2A-A and PP2A-C subunits from H1450 cells using anti- PP2A-C immunoglobulin. Immunoblots of whole-cell lysates using both anti-PP2A-A and anti-PP2A-C show (lane 1) full length PP2A-A (65 kD), truncated ΔPP2A-Aβ (45 kD), and PP2A-C (36 kD). The supernatant after immunoprecipitation with anti-PP2A-C (lane 2) contains PP2A-A, Δ PP2A-Aβ and PP2A-C. The supernatant after washing the immunoprecipitation pellet (lane 3) contains PP2A-A indicating that it is dislodged from the complex during the wash. The immunoprecipitate (lane 4) contains decreased amounts of full-length PP2A-A and PP2A-C, but lacks ΔPP2A-Aβ, suggesting that ΔPP2A-Aβ cannot bind PP2A-C. The control (lane 5) represents the reactivity of anti-PP2A-C immunoglobulin and horse radish peroxidase conjugated anti-immunoglobulin in the absence of cell lysates. (C) Immunoprecipitation of PP2A-A and PP2A-C subunits from normal lung tissue using anti-PP2A-C immunoglobulin. The whole-cell lysate (lane 1) contains PP2A-A (65 kD) and PP2A-C (36 kD). The supernatant after immunoprecipitation with anti-PP2A-C (lane 2) contains PP2A-A and PP2A-C (lane 2). The supernatant after washing (lane 3) lacks PP2A-A indicating that normal PP2A-A remains bound to PP2A-C during wash procedure. The immunoprecipitate contains both PP2A-A and PP2A-C (lane 4). Lane 5 is a control lane with antibodies without cell lysate. The goat anti-PP2A-Aβ immunoglobulin was cross-reactive with the PP2A-Aα isoform as well as PP2A-Aβ.
Figure 3B:
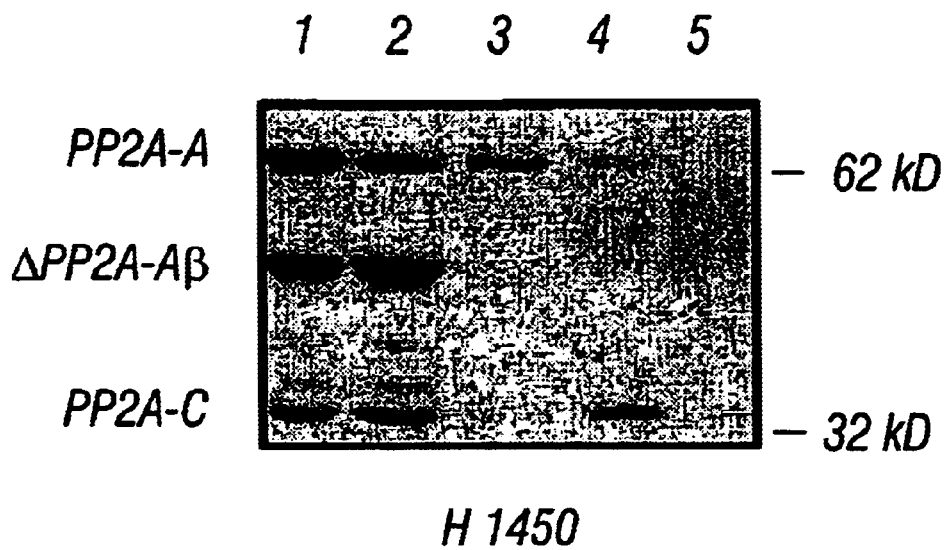
Figure 3C:
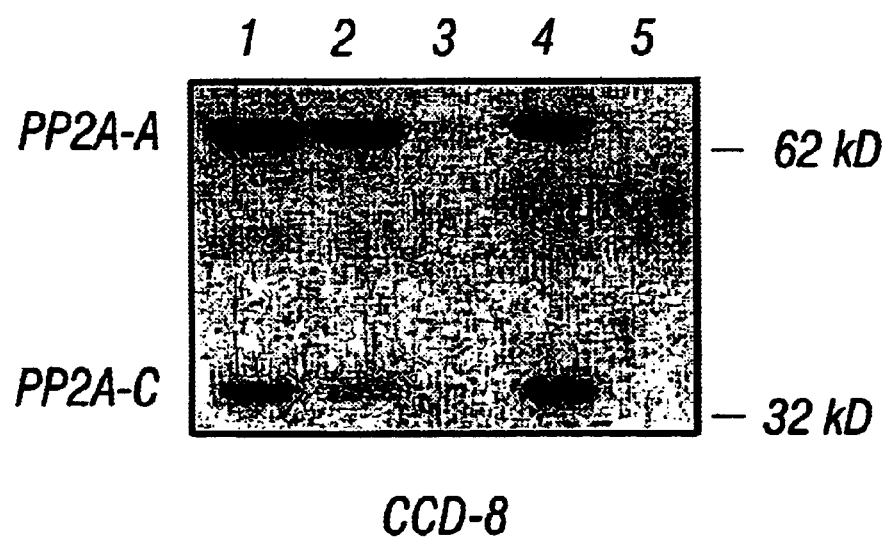
Figure 4B:
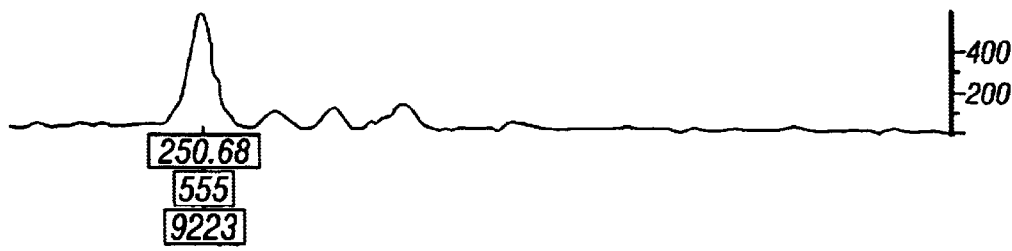
FIG. 4. Analysis of allelic LOH in tumor cell lines and matched controls using automated genoytping procedures. LOH analysis in lung cancer cell lines define a the minimal regions of deletion between D11S1792 and D11S1885 (A), and the region between D11S1647 and NCAM2 (B). Lung cancer cell line numbers and loci are shown at the top of the figure with the sizes, heights and areas of each PCR product shown below the peaks.
Figure 4B:
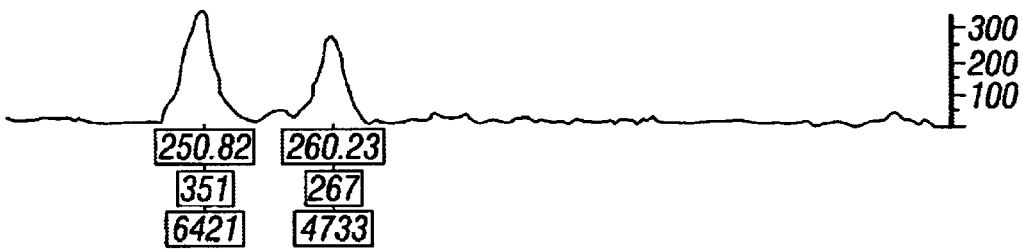
Figure 4B:
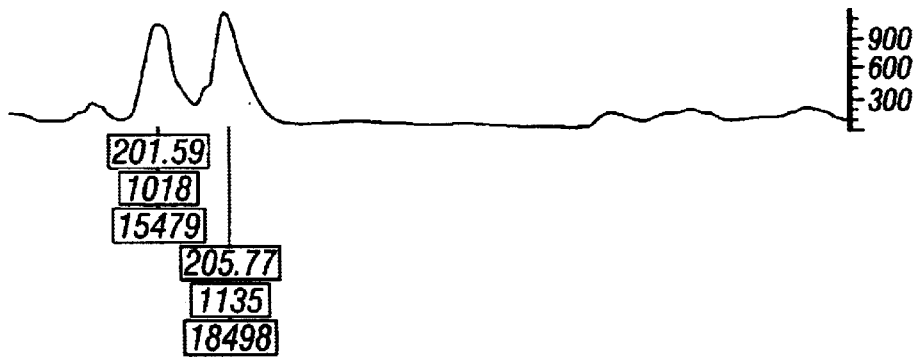
Figure 4B:
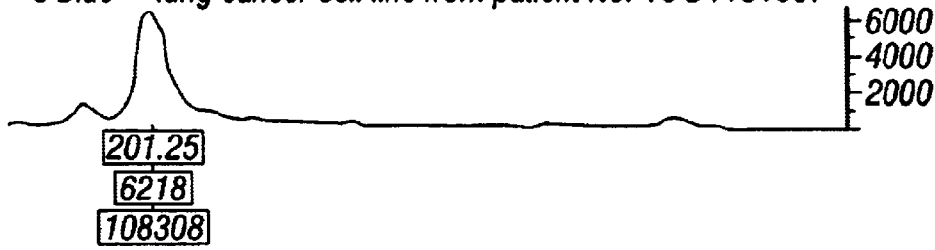

To determine if the sequence alterations in PPP2R1B might produce biochemical changes leading to altered PP2A activity, western blots were carried out using anti-PP2A-Aβ immunoglobulin. Lung cancer line H1450 has two PPP2R1B alterations, a deletion in one PPP2R1B allele and a miss-sense mutation in the other allele of PPP2R1B. Lysates of H1450 were found to contain an immunoreactive truncated PP2A-Aβ protein product of 45 kD in addition to the wild type 65 kD band representing PP2A-A (FIG. 3A). This alteration might be expected to compromise a highly conserved regions of the protein necessary for PP2A-Aβ to form a functional trimer with PP2A-B and PP2A-C (Mumby and Walter, 1993). To determine if PP2A-C binding was altered the PP2A-A, PP2A-B, and PP2A-C subunits were co-immunoprecipitated with a polyclonal antibody directed against the PP2A-C subunit (FIG. 3B). H1450 lysates showed a decreased amount of the PP2A-A and no 45 kD PP2A-Aβ, suggesting that the both the truncated and the missense A subunits have decreased affinity for the C (FIG. 3C). Biochemical assays for total cellular phosphatase activity showed a minor alteration in cell line H1450 compared to control cell lines. Since the regulatory subunits PP2A-A and PP2A-B are thought to control the substrate specificity of the PP2A phosphatase and a vast array of A and B isoforms leads to the combinatoric availability of many PP2A timers with differing specificities, it is not surprising that total cellular phosphatase activity would be unchanged. The precise array of substrates for PP2A-Aβ is not yet known and specific functional activity assays must await substrate identification.

The data described herein define human PPP2R1B alterations in tumor derived cell lines and solid tumors correlating with the high frequency of LOH on chromosome 11q23. 55% (6/11) of the tumors carrying PPP2R1B alterations carry full or partial deletions of one allele combined with deletions or missense alterations in conserved regions of the other allele, leaving the cells functionally null for PPP2R1B. In addition, the genes encoding the many isoforms of the PP2A-B subunit comprise a large and diverse multigene family. At least five isoforms of the PP2A-B subunit have been discovered and map to other regions of the human genome that display frequent LOH in cancer (McCright et al., 1996). This suggests that the search for mutations in other components of the PP2A family and the characterization of the roles PP2A phosphatase plays in tumor development may open exciting new avenues for diagnosis and therapy of cancer.

Example 4

Mapping of Loss of Heterozygosity Surrounding the PP2A-Ab Gene on Chromosome 11q23 in Lung Cancer 17 microsatellite markers spanning the region between D11S940 and ApoC3 were converted to fluorescent-labeled primers in order to analyze DNAs from 28 paired lung cancer cell lines and their corresponding lymphoblastoid cell lines. Allelic loss was determine by comparison of the amplification product sizes with those from matched non-malignant cell lines prepared from the same patient. FIG. 4 shows representative allele comparisons from several analyses.

Figure 5:
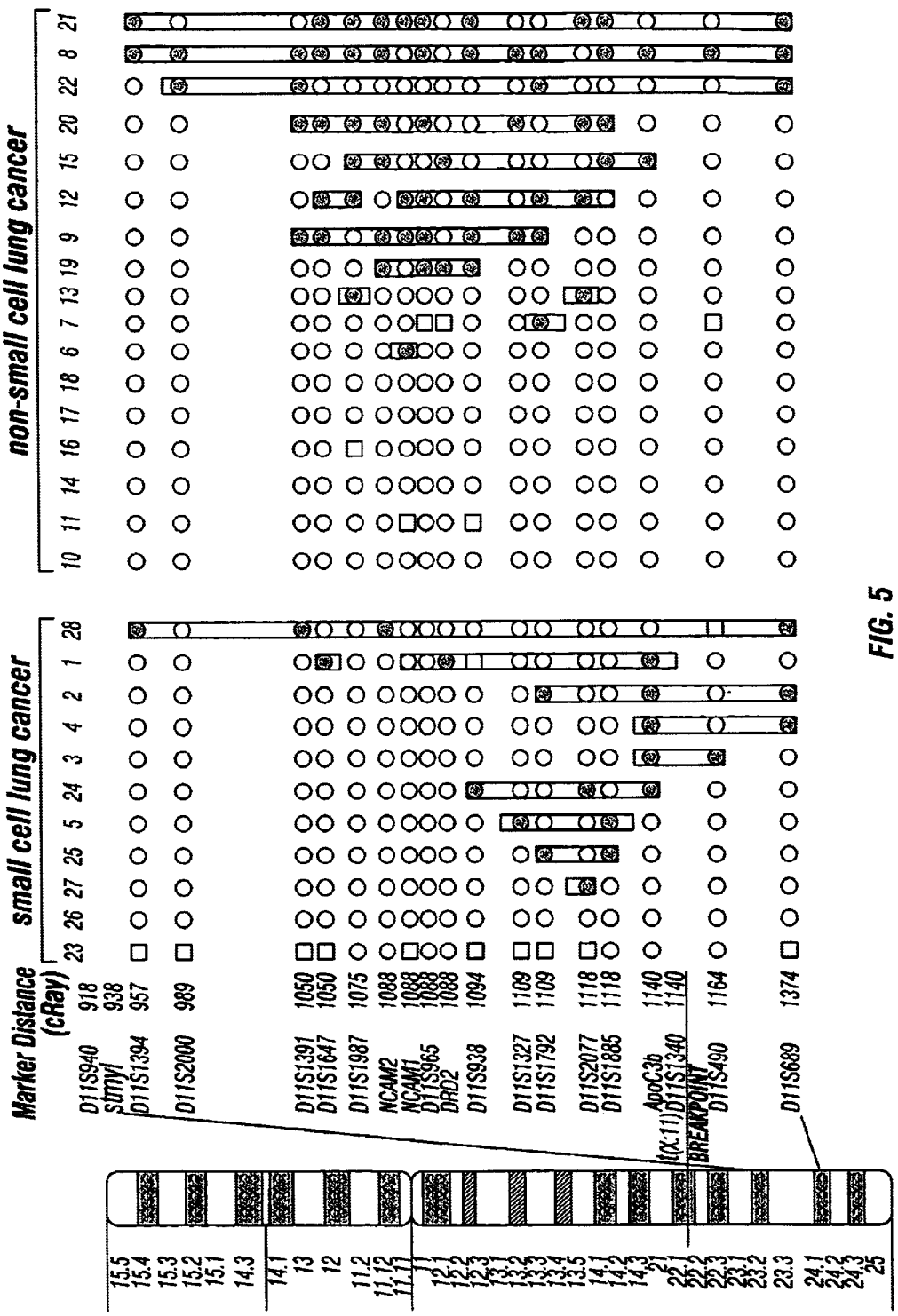
FIG. 5. Schematic representation of LOH allelotyping data on the region between D11S1394 and D11S689 on chromosome 11q22–24 in lung cancer cell lines. This figure represents an ideogram of chromosome 11 and the approximate radiation hybrid "bin" positions of polymorphic markers used in this study. Small cell lung cancers and non-small cell lung cancers are shown denoted on the left and right of the figure. Cell lines are shown in order of LOH frequency from left to right highlighting those cell lines with the highest LOH frequency. Solid circles, LOH; White Circles, Heterozygous with no LOH; dotted circles, non-informative. Solid Square, LOH with genetic alteration, dotted square, non-informative with genetic alteration; white square, no LOH with genetic alteration. The location of the t(X,11) breakpoint, used for defining the location of suppressor oncogene activity is also shown.

The results of the LOH study are shown schematically in FIG. 5 which summarizes the presence or absence of alleles in lung tumor cell lines. The data demonstrate that allelic loss at the region between D11S1394 and D11S689 is quite frequent, occurring in 9 of 11 (81.8%) non-small cell lung cancer cell lines and 11 out of 17 (64.7%) small cell lung cancer cell lines. The LOH frequency overall was 71.4% (20/28). The frequencies of LOH range from 13.3% at D11S2000 to 77.8% at D11S1792 (FIG. 5.)

LOH appeared to cluster into two distinct minimal regions of loss. The first, more telomeric region which is lost in a certain percentage of lung cancer cell lines is exemplified out by case 7, which shows a region of loss bounded by D11S 1327 (1109 cRay) and D11S1885 (1118 cRay). The second, more centomeric region of loss is shown in case 12, which shows LOH for a region bracketed by D11S1391 (1050 cRay) and NCAM2 (1088 cRay). The molecular size of the regions of loss was estimated based on comparisons with entailed physical maps constructed using YAC, BAC and PAC clones (http://gestec.swmed.edu) to be less than 1 Mb.

Allelic loss at the region between D11S1327 and D11S1885 is frequent in both the small cell lung cancer and the non-small cell lung cancer. Out of those 20 lung cancer cell lines which show LOH on the region between D11S1394 and D11S689, 16 of them (80%) show allelic loss in the region between D11S1327 and D11S1885. By analyzing and comparing LOH data at various loci, the minimal region of loss was defined. Cases 7 and 9 show LOH at D11S1792 but not at D11S1885, which indicate the deletion extend at most to D11S 1885 and thus define the telomeric boundary of the region of loss at D11S1885. Case 13 show LOH at D11S2077 but not at D11S938 and D11S1792, which defined the centromeric boundary of the region of loss to D11S1792. The marker D11S2077, which lies between D11S1792 and D11S1885, demonstrates LOH in 75% (6/8) lung cancers.

Allelic loss in the region D11S1391 and NCAM2 is mainly detected in non-small lung cancers (8/17=47.1%). Case 19, heterozygous for D11S1647, shows LOH at NCAM2, D11S965, DRD2 and D11S938. Therefore the minimal region of loss extends at most to D11S1647. Cases 1 and 12, both heterozygous at NCAM2, show LOH at D11S1647, which defines the telomeric boundary of the region of loss to NCAM2. The marker D11S 1987 which lies between D11S1647 and NCAM2, exhibits LOH in 6 out of 9 (66.7%) informative non-small cell lung cancers.

In this study, microsatellite instability on the region between D11S1394 and D11S689 on chromosome 11 were detected in 3 small cell lung cancers (1, 23 and 28) and 3 non-small cell lung cancers (7, 11 and 16) in at least one locus (6/28=21.4%) . Of these 6 lung cancers, 5 cases (1, 7, 11, 23 and 28) show microsatellite instability at multiple loci.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

"A Laboratory Manual" 2nd edition eds., Hogan, Beddington, Costantimi and Long, Cold Spring Harbor Laboratory Press, 1994.
Arai et al., Genomics 35, 196 (1996).
Arcone et al., Nuc. Acids Res. 16(8):3195–3207, 1988.
Baichwal and Sugden, In: Gene Transfer, Kucherlapati R, ed., New York, Plenum Press, pp. 117–148, 1986.
Barany and Merrifield, The Peptides, Gross and Meienhofer, eds., Academic Press, New York, pp. 1–284, 1979.
Bartlett et al., Proc. Natl. Acad. Sci. USA, 93:8852–8857, 1996.
Batterson and Roizman, J. Virol., 46:371–377, 1983.
Bellus, J. Macromol. Sci. Pure Appl. Chem, A311: 1355–1376, 1994.
Benvenisty and Neshif, Proc. Nat. Acad. Sci. USA, 83:9551–9555, 1986.
Berns and Bohenzky, Adv. Virus Res., 32:243–307, 1987.
Berns and Giraud, Curr. Top. Microbiol. Immunol., 218:1–23, 1996.
Berns, Microbiol Rev., 54:316–329, 1990.
Bertran, et al., J Virol., 70 (10)6759–6766, 1996.
Bianchi et al., Nature Genetics, 6:185–192, 1994.
Bigner et al, Cancer Res., 48:405–411, 1988.
Bishop, J. M., Cell, 64:2351–248, 1991.
Brinster et al., Proc. Nat'l Acad. Sci. USA, 82: 4438–4442, 1985.
Brower et al., Cancer Res., 46: 798–806, 1986
Campbell et al, J. Mol. Biol., 180:1–19, 1984.
Capaldi et al., Biochem. Biophys. Res. Comm., 76:425, 1977
Carney et al.,. Cancer Res., 45: 2913–23, 1985.
Carter et al., Proc. Natl. Acad. Sci. USA, 87:8751–8755, 1990.
Chang et al, Hepatology, 14:124A, 1991.
Chen and Okayama, Mol. Cell Biol., 7:2745–2752, 1987.
Coffin, Retroviridae and Their Replication. In: Virology, Fields et al., eds., Raven Press,
New York, pp. 1437–1500, 1990.
Cohen, P., Bioessays, 61–583–588, 1994.
Collet et al., Proc. Natl. Acad. Sci. USA, 75:2021–2024, 1978.
Cook et al., Cell, 27:487–496, 1981.
Couch et al., Am. Rev. Resp. Dis., 88:394–403, 1963.
Culver et al., Science, 256:1550–1552, 1992.
Davey et al., EPO No. 329 822.
Davis, et al., Cancer Res 56 741–4, 1996
DeLuca et al., J. Virol., 56:558–570, 1985.
Dubensky et al., Proc. Nat. Acad. Sci. USA, 81:7529–7533, 1984.
El-Naggar et al., 2067–72, 1996
Elroy-Stein et al., Proc. Nat'l Acad. Sci. USA, 1989.
EP 329 822, Davey et al.
Evans et al., Am. J. Hum. Genet. 59, A66 (1996), abstract.
Fearron and Vogelstein, Cell, 61:759–767, 1990.
Fechheimer et al., Proc. Natl. Acad. Sci. USA, 84:8463–8467, 1987.
Ferkol et al., "FASEB J., 7:1081–1091, 1993.
Fodor et al., Science, 251:767–773, 1991.
Forster and Symons, Cell, 49:211–220, 1987.
Foulds, J. Chronic Dis., 8:2–37, 1958.
Fraley et al., Proc. Natl. Acad. Sci. USA, 76:3348–3352, 1979.
Freifelder, Physical Biochemistry Applications to Biochemistry and Molecular Biology, 2nd ed. Wm. Freeman and Co., New York, N.Y., 1982.
Freshner, Animal Cell Culture: A Practical Approach, 2nd ed., Oxford/New York, IRL Press, Oxford University Press, 1992.
Frohman, In: PCR Protocols: A Guide To Methods And Applications, Academic Press, N.Y., 1990.
Fujiki and Suganuma, Adv. Cancer Res. 61, 143 (1993).
GB Application 2 202 328
Gefter et al, Somatic Cell Genet., 3: 231–236, 1977.
Gerlach et al., Nature London, 328:802–805, 1987.
Ghosh-Choudhury et al., EMBO J., 6:1733–1739, 1987.
Ghosh and Bachhawat, In: Liver Diseases, Targeted Diagnosis and Therapy Using Specific Receptors and Ligands. Wu et al., eds., Marcel Dekker, New York, pp. 87–104, 1991.
Gingeras et al., PCT Application WO 88/10315,
Glorioso et al, Ann. Rev. Microbiol, 49:675–710, 1995.
Goding, 1986, In: Monoclonal Antibodies: Principles and Practice, 2d ed., Academic Press, Orlando, Fla., pp. 60–61, and 71–74, 1986.
Gomez-Foix et al, J. Biol. Chem., 267:25129–25134, 1992.
Gopal, Mol. Cell Biol., 5:1188–1190, 1985.
Gossen and Bujard, Proc. Natl. Acad. Sci. USA, 89:5547–5551, 1992.
Gossen et al, Science, 268:1766–1769, 1995.
Graham and Prevec, In: Methods in Molecular Biology: Gene Transfer and Expression Protocol, E. J. Murray, ed., Humana Press, Clifton, N.J., 7:109–128, 1991.
Graham and van der Eb, Virology, 52:456–467, 1973.
Graham et al., J. Gen. Virol., 36:59–72, 1977.
Grunhaus and Horwitz, Seminar in Virology, 3:237–252, 1992.
Gustafson et al, British Journal of Cancer 70 (1994) 395–7.
Hacia et al, Nature Genetics, 14:441–447, 1996.
Hampton et al, Proc Natl Acad Sci U S A 91 (1994) 6953–7.
Harland and Weintraub, J. Cell Biol., 101:1094–1099, 1985.
Harlow and Lane, Antibodies: A Laboratory manual, Cold Spring Harbor Laboratory, 1988.
Hemmings et al, Biochim 29, 3166 (1990).
Heriche et al., Science 276, 952 (1997).
Hermonat and Muzycska, Proc. Nat. Acad. Sci. USA, 81:6466–6470, 1984.
Hersdorffer et al, DNA Cell Biol., 9:713–723, 1990.
Herz and Gerard, Proc. Nat'l Acad. Sci. USA, 90:2812–2816, 1993.
Holland et al., Virology, 101: 10–18, 1980.
Honess and Roizman, J. Virol., 14:8–19, 1974.
Honess and Roizman, J. Virol., 16:1308–1326, 1975.
Hoon et al., J. Urol., 150(6):2013–2018, 1993.
Hunter, Cell, 64–249–270, 1991.
Innis et al., PCR Protocols, Academic Press, Inc., San Diego Calif., 1990.
Ioannou et al., Nature Genet. 6, 84 (1994).
James, Richard, Schott, Yousry, Clark, Bell, Terwilliger, Hazan, Dubay, Vignal et al, "A radiation hybrid map of 506 STS markers spanning human chromosome 11," Nat Genet 8(1):70–6, 1994.
Johnson et al., Peptide Turn Mimetics" IN: Biotechnology And Pharmacy, Pezzuto et al., eds., Chapman and Hall, New York, 1993.
Joki et al, Human Gene Ther., 6:1507–1513, 1995.
Jones and Shenk, Cell, 13:181–188, 1978.
Jones, et al., Genes Chromosomes Cancer, 9:2, 119–123, 1994.
Kageyama et al., J. Biol. Chem., 262(5):2345–2351, 1987.
Kaneda et al, Science, 243:375–378, 1989.
Karlsson et al., EMBO J., 5:2377–2385, 1986.
Kato et al., J. Biol. Chem., 266:3361–3364, 1991.
Kawabe et al, Nature 385, 454 (1997).
Kearns et al., Gene Ther., 3:748–755, 1996.
Kim and Cook, Proc. Natl. Acad. Sci. USA, 84:8788–8792, 1987.
Klein et al, Nature, 327:70–73, 1987.
Kohler and Milstein, Eur. J. Immunol., 6:511–519, 1976.
Kohler and Milstein, Nature, 256:495497, 1975.
Kotin and Berns, Virol., 170:460–467, 1989.
Kotin et al., Genomics, 10:831–834, 1991.
Kotin et al., Proc. Natl. Acad. Sci. USA, 87:2211–2215, 1990.
Kwoh et al., Proc. Nat. Acad. Sci. USA, 86: 1173, 1989.
Kyte and Doolittle, J. Mol. Biol., 157, 1:105–132, 1982.
Le Gal La Salle et al., Science, 259:988–990, 1993.
Lee et al., Cell 64, 415 (1991).
Lee et al., Science, 235:1394–1399, 1987.
Levrero et al., Gene, 101: 195–202, 1991.
Li and Sun, Cancer Res., 57:2124–2129, 1997.
Li et al. Science 275, 1943 (1997).
Li et al., J. Biol. Chem. 272, 16729 (1997).
Macejak and Sarnow, Nature, 353:90–94, 1991.
Manipulating the Mouse Embryo: A Laboratory Manual, 2nd ed., Hogan et al., eds., Cold Spring Harbor Laboratory Press, 1994.
Mann et al., Cell, 33:153–159, 1983.
Markowitz et al., J. Virol., 62:1120–1124, 1988.
Marshall, Cell 80, 179 (1995).
McCright et al., Genomics 36, 168 (1996).
Merrifield, Science, 232: 341–347, 1986.
Michel and Westhof, J. Mol. Biol., 216:585–610, 1990.
Mizukami et al., Virology, 217:124–130, 1996.
Mulligan, Science, 260:926–932, 1993.
Mumby and Walter, Physiol. Rev. 73, 673 (1993).
Myers, EP 0273085
Nakamura et al., In: Handbook of Experimental Immunology (4th Ed.), Weir, E., Herzenberg, L. A., Blackwell, C., Herzenberg, L. (eds). Vol. 1, Chapter 27, Blackwell Scientific Publ., Oxford, 1987.
Negrini etal., Cancer Res. 54, 1331 (1994).
Nicolas and Rubenstein, In: Vectors: A survey of molecular cloning vectors and their uses, Rodriguez and Denhardt (eds.), Stoneham: Butterworth, pp. 493–513, 1988.
Nicolau et al., Methods Enzymol., 149:157–176, 1987.
Ohara et al., Proc. Nat'l Acad. Sci. USA, 86: 5673–5677, 1989.
Olivierio et al., EMBO J., 6(7):1905–1912, 1987.
Ostrove et al., Virology, 113:532–533, 1981.
Pallas et al., Cell 60, 167 (1990).
Parker, et al.,: A Cancer Journal for Clinicians 47, 5 (1997).
Paskind et al., Virology, 67:242–248, 1975.
PCT/US87/00880
PCT/US89/01025
Pease et al., Proc. Natl. Acad. Sci. USA, 91:5022–5026, 1994.
Perales et al., Proc. Natl. Acad. Sci. 91:4086–4090, 1994.
Pignon et al., Hum. Mutat., 3: 126–132, 1994.
Poli and Cortese, Proc. Natl. Acad. Sci. USA, 86:8202–8206, 1989.
Ponnazhagan et al., Hum. Gene Ther., 8:275–284, 1997a.
Ponnazhagan et al., J. Gen. Virol., 77:1111–1122, 1996.
Post et al., Cell, 24:555–565, 1981.
Potter et al., Proc. Nat. Acad. Sci. USA, 81:7161–7165, 1984.
Prowse and Baumann, Mol Cell Biol, 8(1):42–51, 1988.
Racher et al., Biotechnology Techniques, 9:169–174, 1995.
Ragot et al., Nature, 361:647–650, 1993.
Rasio et al., Cancer Research 55 (1995) 3988–91.
Reinhold-Hurek and Shub, Nature, 357:173–176, 1992.
Remington's Pharmaceutical Sciences, 15th ed., pp. 1035–1038 and 1570–1580.

Renan, Radiother. Oncol., 19:197–218, 1990.
Rich et al., Hum. Gene Ther., 4:461–476, 1993.
Ridgeway, In: Vectors: A survey of molecular cloning vectors and their uses, Rodriguez R L, Denhardt D T, ed., Stoneham:Butterworth, pp. 467–492, 1988.
Rippe et al., Mol. Cell Biol., 10:689–695, 1990.
Ritland et al., Genes. Chromo. Cancer, 12:277–282, 1995.
Roizman and Sears, "An inquiry into the mechanisms of herpes simplex virus latency,"*Annu Rev Microbiol* 41:543–71, 1987.
Ron, Brasier, Habener, "Angiotensinogen gene-inducible enhancer-binding protein 1, a member of a new family of large nuclear proteins that recognize nuclear factor kappa B-binding sites through a zinc finger motif," *Mol Cell Biol* 11(5):2887-95, 1991.
Rosenfeld et al., In vivo transfer of the human cystic fibrosis transmembrane conductance regulator gene to the airway epithelium. Cell, 68:143–155, 1992.
Rosenfeld et al., Science, 252:431–434, 1991.
Roux et al., Proc. Nat'l Acad. Sci. USA, 86:9079–9083, 1989.
Ruediger et al., J. Virol. 68, 123 (1994).
Sambrook et al., In: Molecular Cloning: A Laboratory Manual, 2d Ed., Cold Spring Harbor Laboratory Press, Cold Spring Harbor, N.Y., 1989.
Samulski et al, EMBO J., 10:3941–3950, 1991.
Sarver et al., Science, 247:1222–1225, 1990.
Satoh et al., Mol Carciogenesis 7, 157 (1993).
Saxon, E. S. Srivatsan, E. J. Stanbridge, EMBO J. 5, 3461 (1986).
Scanlon et al., Proc Natl Acad Sci USA, 88:10591–10595, 1991.
Shoemaker et al., Nature Genetics 14:450–456, 1996.
Smith and Moss, Gene, 25:21–28, 1983.
Sontag et al., Cell 75, 887 (1993).
Srivastava et al., J. Virol., 45:555–564, 1983.
Steck et al., Nat. Genet. 15, 356 (1997).
Steck et al., Genes Chromosom. Cancer 712:255–261, 1995.
Stewart and Young, Solid Phase Peptide Synthesis, 2d. ed., Pierce Chemical Co., 1984.
Stratford-Perricaudet and Perricaudet, Gene transfer into animals: the promise of adenovirus. In: Human Gene Transfer, O. Cohen-Haguenauer et al., eds., John Libbey Eurotext, France, pp. 51–61, 1991.
Stratford-Perricaudet et al., Hum. Gene. Ther., 1:241–256, 1990.
Tarn et al., J. Am. Chem. Soc., 105:6442, 1983.
Temin, In: Gene Transfer, Kucherlapati (ed.), New York: Plenum Press, pp. 149–188, 1986.
Tomlinson et al., Eur J Cancer 10 (1996) 1797–802.
Top et al., J. Infect. Dis., 124:155–160, 1971.
Tur-Kaspa et al., Mol. Cell Biol., 6:716–718, 1986.
U. S. Pat. No. 4,554,101
U. S. Pat. No. 4,683,195
U. S. Pat. No. 4,683,202
U. S. Pat. No. 4,800,159
U. S. Pat. No. 4,873,191
U. S. Pat. No. 4,883,750
U. S. Pat. No. 5,252,479
U. S. Pat. No. 5,279,721
U. S. Pat. No. 5,354,855
U. S. Pat. No. 5,672,344
Varnus et al., Cell, 25:23–36, 1981.
Vogelstein, et al., Genes Chromosomes Cancer, 2:2, 159–162, 1990.
Wagner et al., Proc. Natl. Acad. Sci. 87, 9:3410–3414, 1990.
Wagner et al., Science, 260:1510–1513, 1993.
Walker et al., Proc. Nat'l Acad. Sci. USA, 89:392–396 1992.
Walter and Mumby, Biochim. Biophys. Acta. 1155, 207 (1993).
Walther and Stein, J. Mol. Med., 74:379–392, 1996.
Wang et al., Am. J. Hum. Genet. 61, 87 (1997), (abstract).
Weinberg, Biochemistry, 28:8263–8269, 1989.
Weissman et al., Science 236, 175(1987).
Wilson et al., Mol. Cell. Biol., 6181–6191, 1990.
Wong et al., Gene, 10:87–94, 1980.
Wu and Wu, Adv. Drug Delivery Rev., 12:159–167, 1993.
Wu and Wu, J. Biol. Chem., 262:4429–4432, 1987.
Wu and Wu, Biochemistry, 27:887–892, 1988.
Wu et al., Genomics, 4:560, 1989.
Yamaguchi et al., Proc. Natl. Acad. Sci. USA, 91:484–488, 1994.
Yang et al., Proc. Natl. Acad. Sci. USA, 87:9568–9572, 1990.
Zechner et al., Mol. Cell. Biol., 2394–2401, 1988.
Zelenin et al., FEBS Lett., 280:94–96, 1991.

What is claimed is:

1. An isolated polynucleotide comprising a cDNA encoding a polypeptide comprising the sequence of SEQ ID NO:1.

2. The polynucleotide of claim 1, wherein said polynucleotide comprises SEQ ID NO:4.

3. The polynucleotide of claim 1, wherein said polynucleotide further comprises a promoter operably linked to the region encoding SEQ ID NO:1.

4. The polynucleotide of claim 3, further comprising a polyadenylation signal operably linked to said region encoding SEQ ID NO:1.

5. The polynucleotide of claim 4, further comprising an origin of replication.

6. The polynucleotide of claim 5, wherein said polynucleotide is comprised within a viral vector selected from the group consisting of retrovirus, adenovirus, herpesvirus, vaccinia virus and adeno-associated virus.

7. The polynucleotide of claim 6, wherein said polynucleotide is packaged in a virus particle.

8. The polynucleotide of claim 5, wherein said polynucleotide is packaged in a liposome.

* * * * *

UNITED STATES PATENT AND TRADEMARK OFFICE
CERTIFICATE OF CORRECTION

PATENT NO. : 6,743,906 B1
APPLICATION NO. : 09/410416
DATED : June 1, 2004
INVENTOR(S) : Glen A. Evans et al.

It is certified that error appears in the above-identified patent and that said Letters Patent is hereby corrected as shown below:

In column 1, lines 7-9, delete
"The government owns rights in the present invention pursuant to grant number HG-00202-08 from the National Institutes of Health." and insert
--This invention was made with government support under Grant No. HG-00202-08 awarded by the National Institutes of Health. The government has certain rights in the invention.-- therefor.

Signed and Sealed this

Sixth Day of April, 2010

David J. Kappos
*Director of the United States Patent and Trademark Office*

SEQUENCE LISTING

```
<160> NUMBER OF SEQ ID NOS: 19

<210> SEQ ID NO 1
<211> LENGTH: 601
<212> TYPE: PRT
<213> ORGANISM: Homo sapiens

<400> SEQUENCE: 1

Met Ala Gly Ala Ser Glu Leu Gly Thr Gly Pro Gly Ala Ala Gly Gly
 1               5                  10                  15

Asp Gly Asp Asp Ser Leu Tyr Pro Ile Ala Val Leu Ile Asp Glu Leu
                20                  25                  30

Arg Asn Glu Asp Val Gln Leu Arg Leu Asn Ser Ile Lys Lys Leu Ser
            35                  40                  45

Thr Ile Ala Leu Ala Leu Gly Val Glu Arg Thr Arg Ser Glu Leu Leu
        50                  55                  60
```

-continued

```
Pro Phe Leu Thr Asp Thr Ile Tyr Asp Glu Asp Glu Val Leu Leu Ala
 65                  70                  75                  80

Leu Ala Glu Gln Leu Gly Asn Phe Thr Gly Leu Val Gly Gly Pro Asp
             85                  90                  95

Phe Ala His Cys Leu Leu Pro Pro Leu Glu Asn Leu Ala Thr Val Glu
            100                 105                 110

Glu Thr Val Val Arg Asp Lys Ala Val Glu Ser Leu Arg Gln Ile Ser
            115                 120                 125

Gln Glu His Thr Pro Val Ala Leu Glu Ala Tyr Phe Val Pro Leu Val
        130                 135                 140

Lys Arg Leu Ala Ser Gly Asp Trp Phe Thr Ser Arg Thr Ser Ala Cys
145                 150                 155                 160

Gly Leu Phe Ser Val Cys Tyr Pro Arg Ala Ser Asn Ala Val Lys Ala
                165                 170                 175

Glu Ile Arg Gln Gln Phe Arg Ser Leu Cys Ser Asp Asp Thr Pro Met
            180                 185                 190

Val Arg Arg Ala Ala Ser Lys Leu Gly Glu Phe Ala Lys Val Leu
        195                 200                 205

Glu Leu Asp Ser Val Lys Ser Glu Ile Val Pro Leu Phe Thr Ser Leu
        210                 215                 220

Ala Ser Asp Glu Gln Asp Ser Val Arg Leu Leu Ala Val Glu Ala Cys
225                 230                 235                 240

Val Ser Ile Ala Gln Leu Leu Ser Gln Asp Asp Leu Glu Thr Leu Val
                245                 250                 255

Met Pro Thr Leu Arg Gln Ala Ala Glu Asp Lys Ser Trp Arg Val Arg
            260                 265                 270

Tyr Met Val Ala Asp Arg Phe Ser Glu Leu Gln Lys Ala Met Gly Pro
        275                 280                 285

Lys Ile Thr Leu Asn Asp Leu Ile Pro Ala Phe Gln Asn Leu Leu Lys
        290                 295                 300

Asp Cys Glu Ala Glu Val Arg Ala Ala Ala His Lys Val Lys Glu
305                 310                 315                 320

Leu Gly Glu Asn Leu Pro Ile Glu Asp Arg Glu Thr Ile Ile Met Asn
                325                 330                 335

Gln Ile Leu Pro Tyr Ile Lys Glu Leu Val Ser Asp Thr Asn Gln His
            340                 345                 350

Val Lys Ser Ala Leu Ala Ser Val Ile Met Gly Leu Ser Thr Ile Leu
        355                 360                 365

Gly Lys Glu Asn Thr Ile Glu His Leu Leu Pro Leu Phe Leu Ala Gln
    370                 375                 380

Leu Lys Asp Glu Cys Pro Asp Val Arg Leu Asn Ile Ile Ser Asn Leu
385                 390                 395                 400

Asp Cys Val Asn Glu Val Ile Gly Ile Arg Gln Leu Ser Gln Ser Leu
                405                 410                 415

Leu Pro Ala Ile Val Glu Leu Ala Glu Asp Ala Lys Trp Arg Val Arg
            420                 425                 430

Leu Ala Ile Ile Glu Tyr Met Pro Leu Leu Ala Gly Gln Leu Gly Val
        435                 440                 445

Glu Phe Phe Asp Glu Lys Leu Asn Ser Leu Cys Met Ala Trp Leu Val
        450                 455                 460

Asp His Val Tyr Ala Ile Arg Glu Ala Ala Thr Asn Asn Leu Met Lys
465                 470                 475                 480
```

```
Leu Val Gln Lys Phe Gly Thr Glu Trp Ala Gln Asn Thr Ile Val Pro
            485                 490                 495

Lys Val Leu Val Met Ala Asn Asp Pro Asn Tyr Leu His Arg Met Thr
            500                 505                 510

Thr Leu Phe Cys Ile Asn Ala Leu Ser Glu Ala Cys Gly Gln Glu Ile
            515                 520                 525

Thr Thr Lys Gln Met Leu Pro Ile Val Leu Lys Met Ala Gly Asp Gln
            530                 535                 540

Val Ala Asn Val Arg Phe Asn Val Ala Lys Ser Leu Gln Lys Ile Gly
545                 550                 555                 560

Pro Ile Leu Asp Thr Asn Ala Leu Gln Gly Glu Val Lys Pro Val Leu
            565                 570                 575

Gln Lys Leu Gly Gln Asp Glu Asp Met Asp Val Lys Tyr Phe Ala Gln
            580                 585                 590

Glu Ala Ile Ser Val Leu Ala Leu Ala
            595                 600

<210> SEQ ID NO 2
<211> LENGTH: 589
<212> TYPE: PRT
<213> ORGANISM: Xenopus sp.

<400> SEQUENCE: 2

Met Ala Gly Ala Asp Gly Asp Asp Ser Leu Tyr Pro Ile Ala Val Leu
  1               5                  10                  15

Ile Asp Glu Leu Arg Asn Glu Asp Val Gln Leu Arg Leu Asn Ser Ile
                 20                  25                  30

Lys Lys Leu Ser Thr Ile Ala Leu Ala Leu Gly Val Glu Arg Thr Arg
             35                  40                  45

Thr Glu Leu Leu Pro Phe Leu Thr Asp Thr Ile Tyr Asp Glu Asp Glu
         50                  55                  60

Val Leu Leu Ala Leu Ala Glu Gln Leu Gly Ser Phe Thr Ser Leu Val
 65                  70                  75                  80

Gly Gly Ser Glu Phe Val His Cys Leu Leu Pro Pro Leu Glu Ser Leu
                 85                  90                  95

Ala Thr Val Glu Glu Thr Val Val Arg Asp Lys Ala Val Asp Ser Leu
            100                 105                 110

Arg Lys Ile Ser Asn Glu His Ser Pro Val Asp Leu Glu Ala His Phe
            115                 120                 125

Val Pro Leu Val Lys Arg Leu Ala Ser Gly Asp Trp Phe Thr Ser Arg
            130                 135                 140

Thr Ser Ala Cys Gly Leu Phe Ser Val Cys Tyr Pro Arg Val Ser Ser
145                 150                 155                 160

Thr Val Lys Ala Glu Ile Arg Gln His Phe Arg Asn Leu Cys Ser Asp
            165                 170                 175

Asp Thr Pro Ile Val Arg Arg Ala Ala Ser Lys Leu Gly Glu Phe
            180                 185                 190

Ala Lys Val Leu Glu Leu Glu Tyr Val Lys Asn Asp Leu Ile Pro Leu
            195                 200                 205

Phe Thr Asn Leu Ala Ser Asp Glu Gln Asp Ser Val Arg Leu Leu Ala
            210                 215                 220

Val Glu Ala Cys Val Asn Ile Ala Glu Leu Leu Pro Glu Glu Asp Leu
225                 230                 235                 240

Glu Ala His Val Leu Pro Thr Leu Arg Gln Ala Thr Glu Asp Lys Ser
            245                 250                 255
```

-continued

```
Cys Gly Val Arg Tyr Met Val Ala Asp Lys Phe Ser Glu Leu Gln Lys
            260                 265                 270
Ala Val Gly Pro Glu Ile Thr Lys Asn Asp Leu Val Pro Ala Phe Gln
            275                 280                 285
Asn Leu Leu Lys Asp Cys Glu Ala Val Arg Ala Ala Ala His
            290                 295                 300
Lys Val Lys Glu Phe Cys Glu Asn Leu Pro Asp Asp Gly Arg Glu Thr
305                 310                 315                 320
Ile Ile Met Ser His Ile Leu Pro Tyr Val Lys Glu Leu Val Ser Asp
                    325                 330                 335
Thr Asn Gln His Val Lys Ser Ala Leu Pro Ser Val Ile Met Gly Leu
            340                 345                 350
Ser Thr Ile Leu Gly Lys Asp Asn Thr Ile Glu His Leu Leu Pro Leu
            355                 360                 365
Phe Leu Ala Gln Leu Lys Asp Glu Cys Pro Glu Val Arg Leu Asn Ile
            370                 375                 380
Ile Ser Asn Leu Asp Cys Val Asn Glu Val Ile Gly Ile Arg Gln Leu
385                 390                 395                 400
Ser Gln Ser Leu Leu Pro Ala Ile Val Glu Leu Ala Glu Asp Thr Lys
                    405                 410                 415
Trp Arg Val Arg Leu Ala Ile Ile Glu Tyr Met Pro Leu Leu Ala Gly
            420                 425                 430
Gln Leu Gly Val Glu Phe Phe Asp Glu Lys Leu Asn Ser Leu Cys Met
            435                 440                 445
Ala Trp Leu Val Asp His Val Tyr Ala Ile Arg Glu Ala Ala Thr Asn
            450                 455                 460
Asn Leu Met Lys Leu Val Glu Lys Phe Gly Ala Glu Trp Ala Gln Asn
465                 470                 475                 480
Thr Ile Val Pro Lys Val Leu Ala Met Ala Asn Asp Pro Asn Tyr Leu
                    485                 490                 495
His Arg Met Thr Thr Leu Phe Cys Val Asn Ala Leu Ser Glu Ala Cys
            500                 505                 510
Gly Lys Glu Ile Thr Thr Lys Leu Met Leu Pro Ile Val Leu Lys Met
            515                 520                 525
Ala Ala Asp Gln Asp Ala Asn Val Arg Phe Asn Val Ala Arg Ser Leu
            530                 535                 540
Gln Arg Ile Gly Pro Val Leu Asp Asp Thr Thr Leu Gln Ser Asp Val
545                 550                 555                 560
Lys Pro Ile Leu Leu Lys Leu Gly Gln Asp Glu Asp Met Asp Val Lys
                    565                 570                 575
Tyr Phe Ala Gln Glu Ala Met Thr Val Leu Ala Leu Ala
            580                 585

<210> SEQ ID NO 3
<211> LENGTH: 602
<212> TYPE: PRT
<213> ORGANISM: Sus scrofa

<400> SEQUENCE: 3

Asn Ser Ala Gly Ala Ala Ala Pro Gly Thr Gly Pro Val Ala Ala Gly
  1               5                  10                  15
Gly Asp Gly Asp Asp Ser Leu Tyr Pro Ile Ala Val Leu Ile Asp Glu
            20                  25                  30
Leu Arg Asn Glu Asp Val Gln Leu Arg Leu Asn Ser Ile Lys Lys Leu
```

```
              35                  40                  45
Ser Thr Ile Ala Leu Ala Leu Gly Val Glu Arg Thr Arg Thr Glu Leu
     50                  55                  60

Leu Pro Phe Leu Thr Asp Thr Ile Tyr Asp Glu Asp Glu Val Leu Leu
 65                  70                  75                  80

Ala Leu Ala Glu Gln Leu Gly Asn Phe Thr Gly Leu Val Gly Gly Pro
                 85                  90                  95

Asp Phe Ala His Cys Leu Leu Pro Pro Leu Glu Ser Leu Ala Thr Val
                100                 105                 110

Glu Glu Thr Val Val Arg Asp Lys Ala Val Glu Ser Leu Arg Gln Ile
            115                 120                 125

Ser Gln Glu His Thr Pro Val Ala Leu Glu Ala His Phe Val Pro Leu
130                 135                 140

Val Lys Arg Leu Ala Ser Gly Asp Trp Phe Thr Ser Arg Thr Ser Ala
145                 150                 155                 160

Cys Gly Leu Phe Ser Val Cys Tyr Pro Arg Ala Ser Asn Ala Val Lys
                165                 170                 175

Ala Glu Ile Arg Gln His Phe Arg Ser Leu Cys Ser Asp Asp Thr Pro
            180                 185                 190

Met Val Arg Arg Ala Ala Ser Lys Leu Gly Glu Phe Ala Lys Val
            195                 200                 205

Leu Glu Leu Asp Ser Val Lys Ser Glu Ile Val Pro Leu Phe Thr Asn
210                 215                 220

Leu Ala Ser Asp Glu Gln Asp Ser Val Arg Leu Leu Ala Val Glu Ala
225                 230                 235                 240

Cys Val Ser Ile Ala Gln Leu Leu Ser Gln Asp Asp Leu Glu Ala Leu
                245                 250                 255

Val Met Pro Thr Leu Arg Gln Ala Ala Glu Asp Lys Ser Trp Arg Val
            260                 265                 270

Arg Tyr Met Val Ala Asp Lys Phe Ser Glu Leu Gln Arg Ala Val Gly
        275                 280                 285

Pro Lys Ile Thr Leu Asn Asp Leu Ile Pro Ala Phe Gln Asn Leu Leu
    290                 295                 300

Lys Asp Cys Glu Ala Glu Val Arg Ala Ala Ala His Lys Val Lys
305                 310                 315                 320

Glu Leu Cys Glu Asn Leu Pro Ile Glu Gly Arg Glu Thr Ile Ile Met
                325                 330                 335

Asn Gln Ile Leu Pro Cys Ile Lys Glu Leu Val Ser Asp Thr Asn Gln
            340                 345                 350

His Val Lys Ser Ala Leu Ala Ser Val Ile Met Gly Leu Ser Thr Ile
        355                 360                 365

Leu Gly Lys Glu Asn Thr Ile Glu His Leu Leu Pro Leu Phe Leu Ala
    370                 375                 380

Gln Leu Lys Asp Glu Cys Pro Glu Val Arg Leu Asn Ile Ile Ser Asn
385                 390                 395                 400

Leu Asp Cys Val Asn Glu Val Ile Gly Ile Arg Gln Leu Ser Gln Ser
                405                 410                 415

Leu Leu Pro Ala Ile Val Glu Leu Ala Glu Asp Ala Lys Trp Arg Val
            420                 425                 430

Arg Leu Ala Ile Ile Glu Tyr Met Pro Leu Leu Ala Gly Gln Leu Gly
        435                 440                 445

Val Glu Phe Phe Asp Glu Lys Leu Asn Ser Leu Cys Met Ala Trp Leu
    450                 455                 460
```

-continued

```
Val Asp His Val Tyr Ala Ile Arg Glu Ala Ala Thr Asn Asn Leu Met
465                 470                 475                 480

Lys Leu Val Gln Lys Phe Gly Thr Glu Trp Ala Gln Asn Thr Ile Val
            485                 490                 495

Pro Lys Val Leu Val Met Ala Asn Asp Pro Asn Tyr Leu His Arg Met
            500                 505                 510

Thr Thr Leu Phe Cys Ile Asn Val Leu Ser Glu Ala Cys Gly Gln Glu
            515                 520                 525

Ile Thr Thr Lys Gln Met Leu Pro Ile Val Leu Lys Met Ala Gly Asp
            530                 535                 540

Gln Val Ala Asn Val Arg Phe Asn Val Ala Lys Ser Leu Gln Lys Ile
545                 550                 555                 560

Gly Pro Ile Leu Asp Thr Asp Ala Leu Gln Glu Glu Val Lys Pro Val
            565                 570                 575

Leu Gln Lys Leu Gly Gln Asp Glu Asp Met Asp Val Lys Tyr Phe Ala
            580                 585                 590

Gln Glu Ala Ile Ser Val Leu Ala Leu Ala
            595                 600
```

<210> SEQ ID NO 4
<211> LENGTH: 1922
<212> TYPE: DNA
<213> ORGANISM: Homo sapiens

<400> SEQUENCE: 4

```
gggtgaccag cagcaggagg agaaagaaca tggcgggcgc atcagagctc gggaccggcc    60
caggagcagc gggtggagat ggagatgatt cgctataccc gatcgcggtt ttaatcgacg   120
agctccgcaa tgaagacgtg cagctccgac tcaacagtat taagaagtta tcaacaattg   180
ccctagcact tggagtagaa aggacccgaa gtgaattgtt gccatttctt acagatacaa   240
tttatgatga agatgaggta ctattagctc ttgctgagca gctgggaaat ttcactggcc   300
tagtgggagg tcctgacttt gcccactgtc tgctgcctcc tttggaaaat ctggcaactg   360
tggaagagac tgttgttcgt gacaaggctg tggagtccct gagacagatc tcccaggagc   420
atactcctgt tgctctggaa gcttattttg tacctctggt gaaacgctta gcaagtgggg   480
attggttcac ctctcgcaca tctgcatgtg gtttgttcag cgtttgctat cccagggcat   540
caaatgctgt taaagcagaa atcagacagc aattccgttc cttgtgctca gatgacacac   600
caatggtacg acgtgctgct gcttccaaat tgggtgaatt tgcaaaagtt ttggaattag   660
acagtgtgaa aagtgaaatt gttccactgt tcactagtct agcttcagat gaacaggatt   720
cagtgcgcct ccttgctgtg gaagcttgtg tcagtattgc ccagttattg tctcaggatg   780
accttgagac tttggtgatg cctacacttc gacaagcagc agaagataaa tcttggcgcg   840
ttcgctatat ggtggctgac agattttcag agctccagaa agccatgggt cctaaaatca   900
ccctaaatga cctcatcccc gcctttcaga acctacttaa agactgtgaa gctgaagtcc   960
gggcagctgc tgcccacaaa gtaaaagaac ttggtgagaa cttgcccatt gaagatagag  1020
agaccataat tatgaatcaa attctgcctt atataaagga attagtatcc gataccaatc  1080
aacatgtcaa atcggctcta gcttctgtaa ttatgggatt gtctactatt ttgggcaaag  1140
aaaataccat tgaacatctt ctacctcttt tcttagctca gttaaaggat gagtgtcctg  1200
acgttcgttt gaatatcatc tccaatttgg attgtgtaaa tgaagtgatt ggaatccgtc  1260
agctctctca gtctctcctt cctgccatag tggagctggc agaagatgcc aaatggaggg  1320
```

-continued

```
tccgcctggc catcattgag tatatgccgc tgctggcagg ccagctgggt gtggaattct    1380
ttgatgaaaa gctgaattct ttatgtatgg cttggctcgt ggaccatgta tacgccatcc    1440
gagaagctgc caccaacaac ctcatgaaac tagttcagaa gtttggtaca gagtgggccc    1500
aaaatactat tgttcccaaa gtgttagtaa tggcaaatga tcctaattac ttgcatagaa    1560
tgaccacttt attctgcatt aatgcactgt ctgaggcctg tggtcaggaa ataactacta    1620
agcaaatgct gcccatcgta ttaaaaatgg caggagacca agtagcaaat gttcgcttca    1680
atgtggccaa atctctacaa aagattggac caattctaga taccaatgct ttacagggag    1740
aagtgaagcc agtactacag aagttaggtc aagatgaaga catggatgtc aaatactttg    1800
cacaggaagc tataagtgtt cttgcattgg cataatgagg agcaggaggg aaaaggcctt    1860
tactagattc ttgtcacaaa tttctagtca atgtgttctt aactgggtgg agaaagaatg    1920
ga                                                                   1922
```

<210> SEQ ID NO 5
<211> LENGTH: 589
<212> TYPE: PRT
<213> ORGANISM: Homo sapiens

<400> SEQUENCE: 5

```
Met Ala Ala Asp Gly Asp Asp Ser Leu Tyr Pro Ile Ala Val Leu
 1               5                  10                  15

Ile Asp Glu Leu Arg Asn Glu Asp Val Gln Leu Arg Leu Asn Ser Ile
            20                  25                  30

Lys Lys Leu Ser Thr Ile Ala Leu Ala Leu Gly Val Glu Arg Thr Arg
        35                  40                  45

Ser Glu Leu Leu Pro Phe Leu Thr Asp Thr Ile Tyr Asp Glu Asp Glu
    50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95

Ala Thr Val Glu Glu Thr Val Val Arg Asp Lys Ala Val Glu Ser Leu
            100                 105                 110

Arg Ala Ile Ser His Glu His Ser Pro Ser Asp Leu Glu Ala His Phe
        115                 120                 125

Val Pro Leu Val Lys Arg Leu Ala Gly Gly Asp Trp Phe Thr Ser Arg
    130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ala Ser Lys Leu Gly Glu Phe
            180                 185                 190

Ala Lys Val Leu Glu Leu Asp Asn Val Lys Ser Glu Ile Ile Pro Met
        195                 200                 205

Phe Ser Asn Leu Ala Ser Asp Glu Gln Asp Ser Val Arg Leu Leu Ala
    210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255
```

-continued

```
Trp Ala Val Arg Tyr Met Val Ala Asp Lys Phe Thr Glu Leu Gln Lys
            260                 265                 270

Ala Val Gly Pro Glu Ile Thr Lys Thr Asp Leu Val Pro Ala Phe Gln
            275                 280                 285

Asn Leu Met Lys Asp Cys Glu Ala Glu Val Arg Ala Ala Ser His
            290                 295                 300

Lys Val Lys Glu Phe Cys Glu Asn Leu Ser Ala Asp Cys Arg Glu Asn
305                 310                 315                 320

Val Ile Met Ser Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
            355                 360                 365

Phe Leu Ala Gln Leu Lys Asp Glu Cys Pro Glu Val Arg Leu Asn Ile
            370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
            420                 425                 430

Gln Leu Gly Val Glu Phe Phe Asp Glu Lys Leu Asn Ser Leu Cys Met
            435                 440                 445

Ala Trp Leu Val Asp His Val Tyr Ala Ile Arg Glu Ala Ala Thr Ser
            450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
            500                 505                 510

Gly Gln Asp Ile Thr Thr Lys His Met Leu Pro Thr Val Leu Arg Met
            515                 520                 525

Ala Gly Asp Pro Val Ala Asn Val Arg Phe Asn Val Ala Lys Ser Leu
            530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
            580                 585
```

<210> SEQ ID NO 6
<211> LENGTH: 18
<212> TYPE: DNA
<213> ORGANISM: Homo sapiens

<400> SEQUENCE: 6
ggtgaccagc agcaggag                                                   18

<210> SEQ ID NO 7
<211> LENGTH: 21
<212> TYPE: DNA
<213> ORGANISM: Homo sapiens

```
<400> SEQUENCE: 7
gcttggatga gatcttgaag g                                              21

<210> SEQ ID NO 8
<211> LENGTH: 21
<212> TYPE: DNA
<213> ORGANISM: Homo sapiens

<400> SEQUENCE: 8
gcgcatcaga gctcgggacc g                                              21

<210> SEQ ID NO 9
<211> LENGTH: 27
<212> TYPE: DNA
<213> ORGANISM: Homo sapiens

<400> SEQUENCE: 9
ccattctttc tccacccagt taagaac                                        27

<210> SEQ ID NO 10
<211> LENGTH: 24
<212> TYPE: DNA
<213> ORGANISM: Homo sapiens

<400> SEQUENCE: 10
tcacttcggg tcctttctac tcca                                           24

<210> SEQ ID NO 11
<211> LENGTH: 21
<212> TYPE: DNA
<213> ORGANISM: Homo sapiens

<400> SEQUENCE: 11
cttcattgcg gagctcgtcg a                                              21

<210> SEQ ID NO 12
<211> LENGTH: 16
<212> TYPE: DNA
<213> ORGANISM: Homo sapiens

<400> SEQUENCE: 12
gatgaacagg cactgt                                                    16

<210> SEQ ID NO 13
<211> LENGTH: 17
<212> TYPE: DNA
<213> ORGANISM: Homo sapiens

<400> SEQUENCE: 13
gatgaacagg attcagt                                                   17

<210> SEQ ID NO 14
<211> LENGTH: 14
<212> TYPE: DNA
<213> ORGANISM: Homo sapiens

<400> SEQUENCE: 14
tcactgacct agtc                                                      14

<210> SEQ ID NO 15
<211> LENGTH: 13
<212> TYPE: DNA
<213> ORGANISM: Homo sapiens
```

-continued

```
<400> SEQUENCE: 15
tcactggcct agt                                                              13

<210> SEQ ID NO 16
<211> LENGTH: 16
<212> TYPE: DNA
<213> ORGANISM: Homo sapiens

<400> SEQUENCE: 16
cagagctccg gaccgg                                                           16

<210> SEQ ID NO 17
<211> LENGTH: 16
<212> TYPE: DNA
<213> ORGANISM: Homo sapiens

<400> SEQUENCE: 17
cagagctcgg gaccgg                                                           16

<210> SEQ ID NO 18
<211> LENGTH: 16
<212> TYPE: DNA
<213> ORGANISM: Homo sapiens

<400> SEQUENCE: 18
atataaagtg tcctga                                                           16

<210> SEQ ID NO 19
<211> LENGTH: 16
<212> TYPE: DNA
<213> ORGANISM: Homo sapiens

<400> SEQUENCE: 19
atataaagga attagt                                                           16
```